US010136960B2

(12) United States Patent
Fleenor

(10) Patent No.: US 10,136,960 B2
(45) Date of Patent: Nov. 27, 2018

(54) HAND-HELD ELECTROSURGICAL INSTRUMENT

(71) Applicant: Richard P. Fleenor, Englewood, CO (US)

(72) Inventor: Richard P. Fleenor, Englewood, CO (US)

(\*) Notice: Subject to any disclaimer, the term of this patent is extended or adjusted under 35 U.S.C. 154(b) by 0 days.

(21) Appl. No.: 14/997,911

(22) Filed: Jan. 18, 2016

(65) Prior Publication Data

US 2016/0278874 A1 Sep. 29, 2016

Related U.S. Application Data

(63) Continuation-in-part of application No. 14/561,082, filed on Dec. 4, 2014, and a continuation-in-part of application No. 13/405,923, filed on Feb. 27, 2012, now Pat. No. 9,237,922.

(60) Provisional application No. 61/911,864, filed on Dec. 4, 2013, provisional application No. 61/447,562, filed on Feb. 28, 2011.

(51) Int. Cl.
*A61B 90/30* (2016.01)
*A61B 18/14* (2006.01)
*A61B 18/00* (2006.01)
*A61B 18/12* (2006.01)

(52) U.S. Cl.
CPC .......... *A61B 90/30* (2016.02); *A61B 18/1402* (2013.01); *A61B 2018/0091* (2013.01); *A61B 2018/00916* (2013.01); *A61B 2018/1226* (2013.01); *A61B 2090/309* (2016.02); *A61B 2218/008* (2013.01)

(58) Field of Classification Search
CPC ...... A61B 19/5202; A61B 2018/00916; A61B 2019/4836; A61B 2019/507; A61B 2019/521
See application file for complete search history.

(56) References Cited

U.S. PATENT DOCUMENTS

| 4,562,838 A | 1/1986 | Walker |
| 4,688,569 A | 8/1987 | Rabinowitz |
| 5,061,268 A | 10/1991 | Fleenor |
| 5,098,430 A | 3/1992 | Fleenor |
| 5,246,440 A | 9/1993 | Van Noord |
| 5,306,238 A | 4/1994 | Fleenor |

(Continued)

FOREIGN PATENT DOCUMENTS

WO 2004/054626 A2 7/2004

*Primary Examiner* — Deborah Malamud
(74) *Attorney, Agent, or Firm* — Marsh Fischmann & Breyfogle LLP; Thomas R. Marsh

(57) ABSTRACT

Electrosurgical instruments and associated methods are provided. An electrosurgical instrument may include one or more light emitters that comprise a light source in operative communication with a power supply supportably interconnected to a handle portion. The instrument may have a toggle member with one or more selectable positions that may selectively activate any of one or more operational states of an electrosurgical electrode comprising the instrument. The toggle member may selectively activate the light emitter(s) provided on the instrument alone and/or in conjunction with the activation of one or more operational state. The handle portion may include an elastomeric handle portion that extends continuously along the handle portion and over the toggle member to seal the handle portion.

20 Claims, 20 Drawing Sheets

(56) References Cited

U.S. PATENT DOCUMENTS

| | | | |
|---|---|---|---|
| 5,484,435 | A | 1/1996 | Fleenor et al. |
| 5,843,080 | A | 12/1998 | Fleenor et al. |
| 6,053,910 | A | 4/2000 | Fleenor |
| 6,083,221 | A | 7/2000 | Fleenor et al. |
| 6,214,000 | B1 | 4/2001 | Fleenor et al. |
| 6,454,764 | B1 | 9/2002 | Fleenor et al. |
| 6,562,032 | B1 | 5/2003 | Ellman et al. |
| 6,648,902 | B2 | 11/2003 | Colgan et al. |
| 6,666,859 | B1 | 12/2003 | Fleenor et al. |
| 7,083,601 | B1 | 8/2006 | Cosmescu |
| 7,166,102 | B2 | 1/2007 | Fleenor et al. |
| 7,367,971 | B2 | 5/2008 | Fleenor et al. |
| 8,690,872 | B2 | 4/2014 | Jayaraj |
| 8,882,768 | B2 | 11/2014 | Greep et al. |
| 2002/0111624 | A1* | 8/2002 | Witt .................. A61B 18/1442 606/51 |
| 2007/0049927 | A1 | 3/2007 | Saltzman |
| 2009/0076504 | A1 | 3/2009 | Schnitzler |
| 2009/0209979 | A1* | 8/2009 | Yates ............... A61B 17/07207 606/143 |
| 2010/0145333 | A1 | 6/2010 | Dethier et al. |
| 2012/0283728 | A1 | 11/2012 | Cosmescu |
| 2014/0276763 | A1 | 9/2014 | Greep et al. |
| 2014/0293590 | A1 | 10/2014 | Pathy |

* cited by examiner

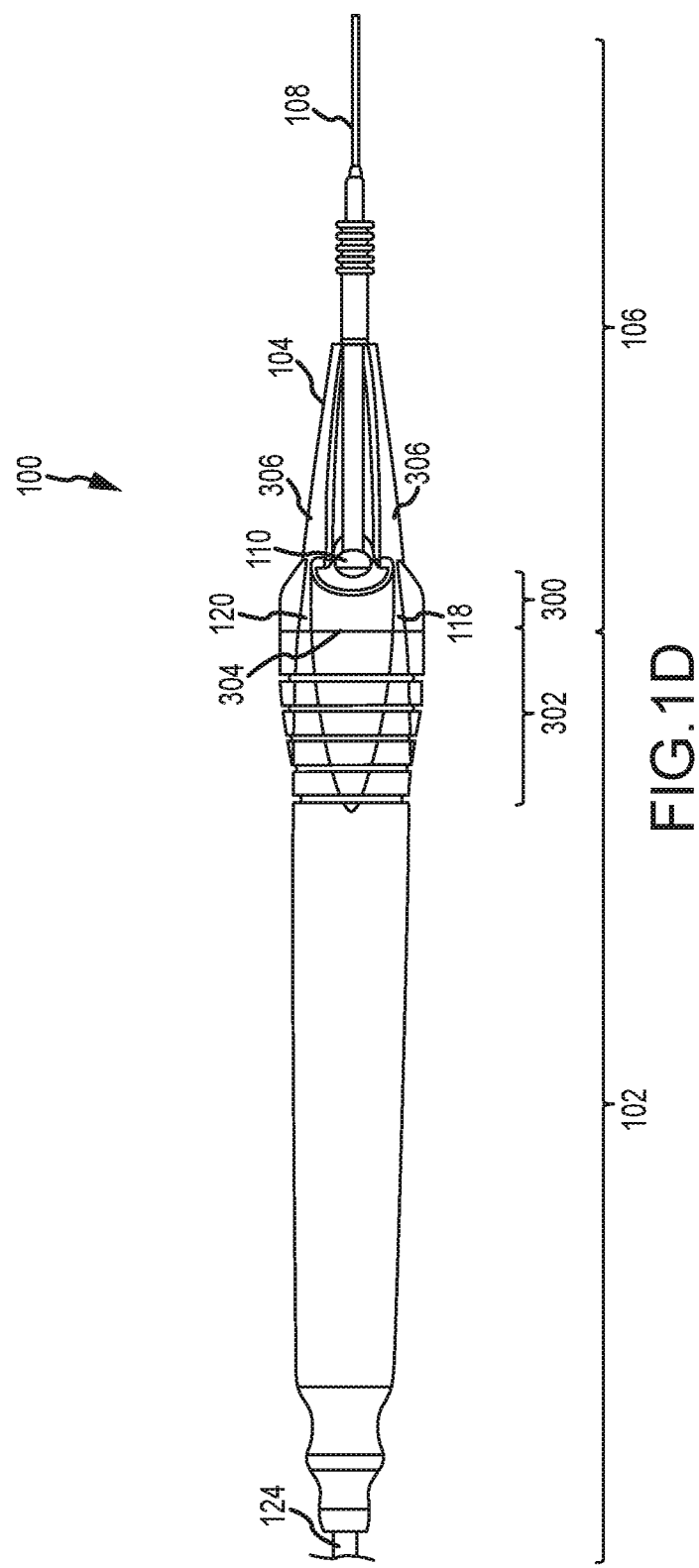

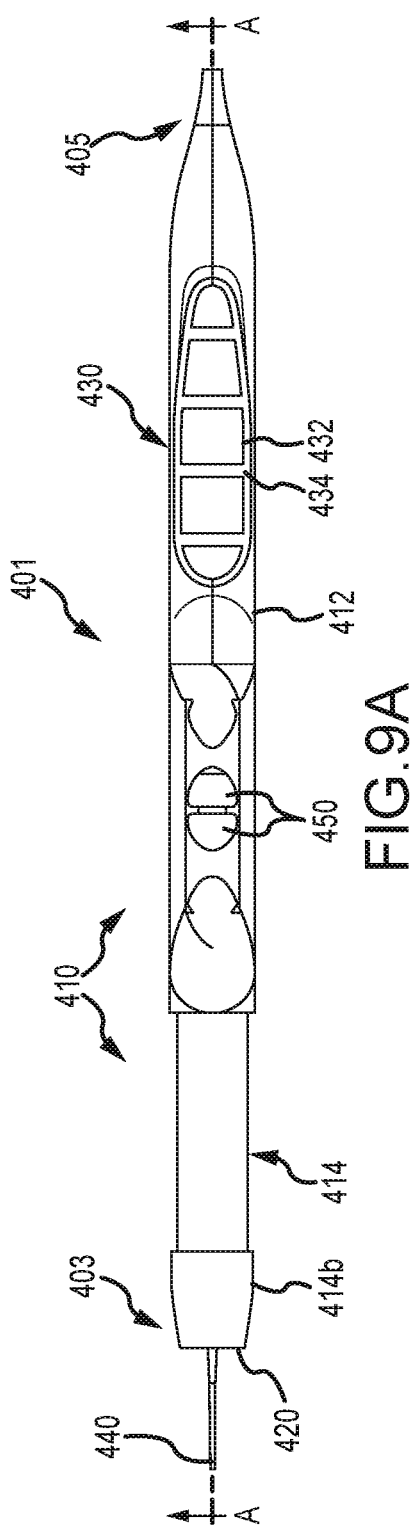
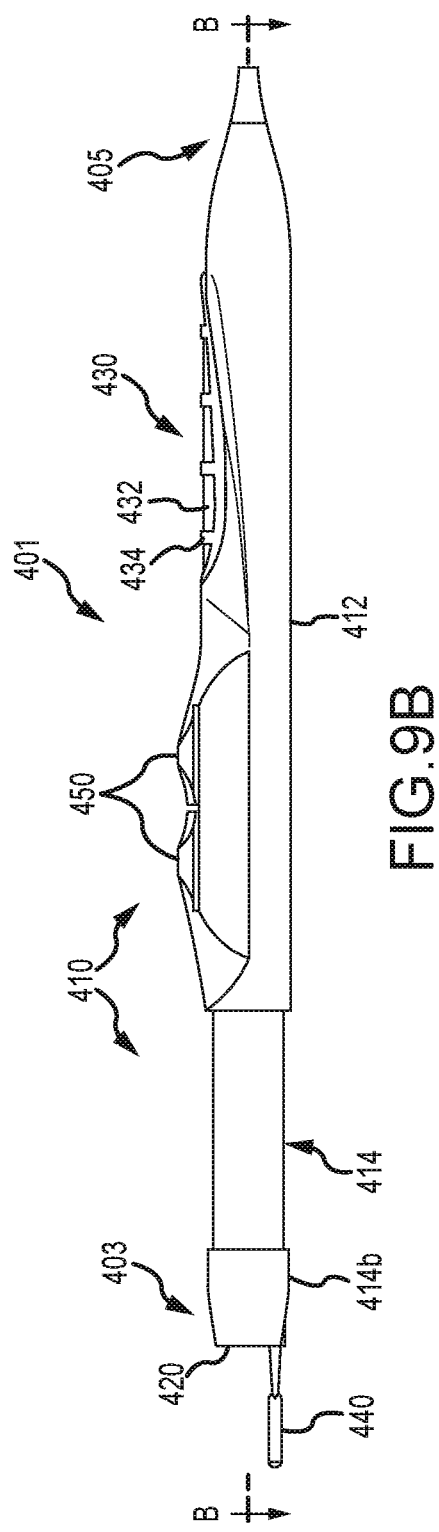
FIG.9A
FIG.9B

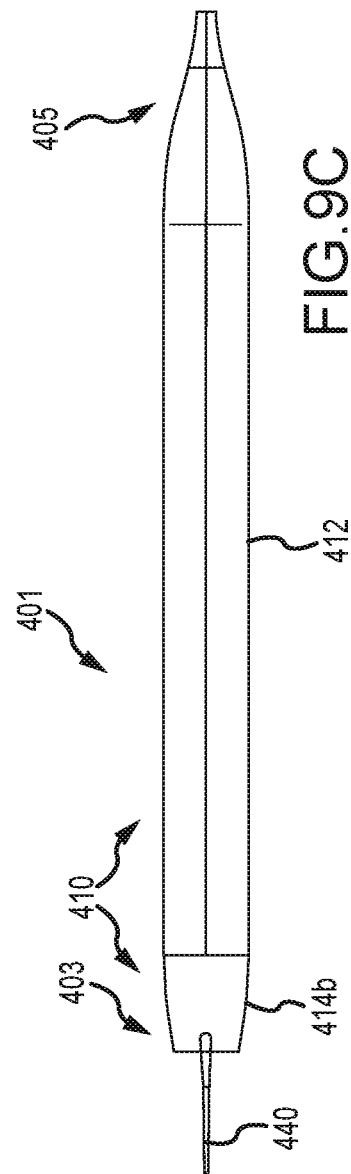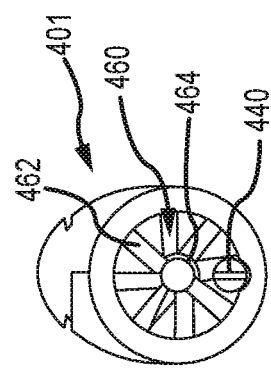

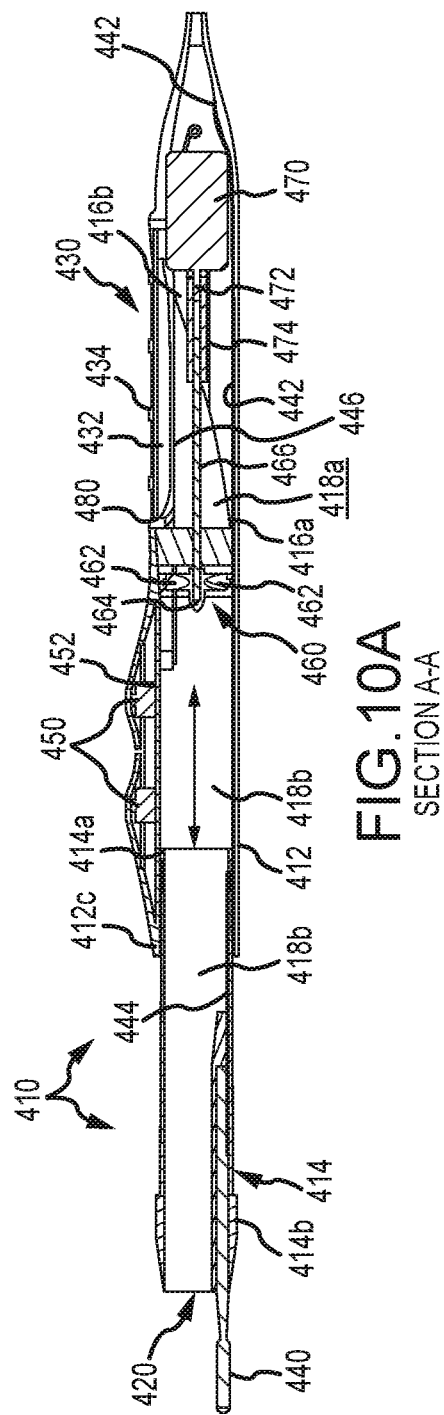
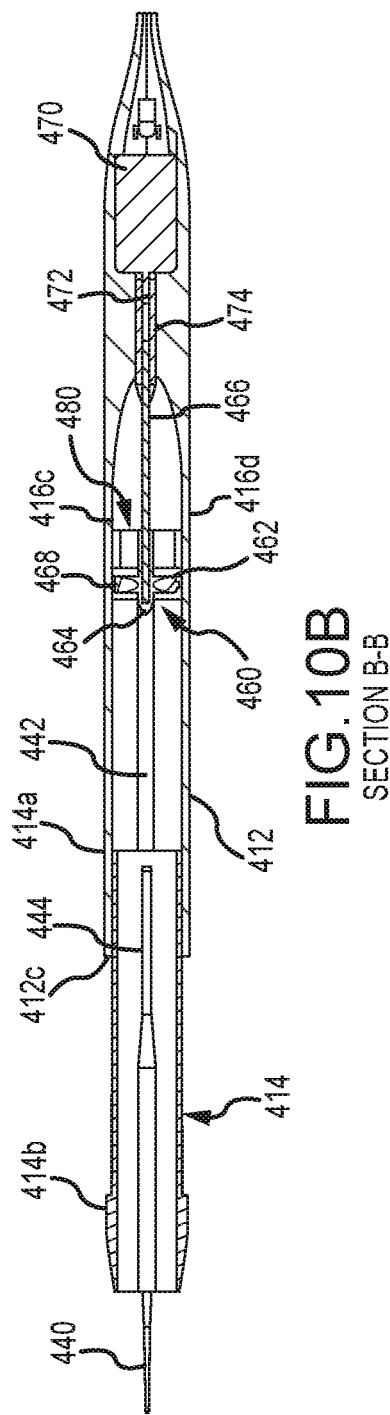
FIG. 10A SECTION A-A
FIG. 10B SECTION B-B

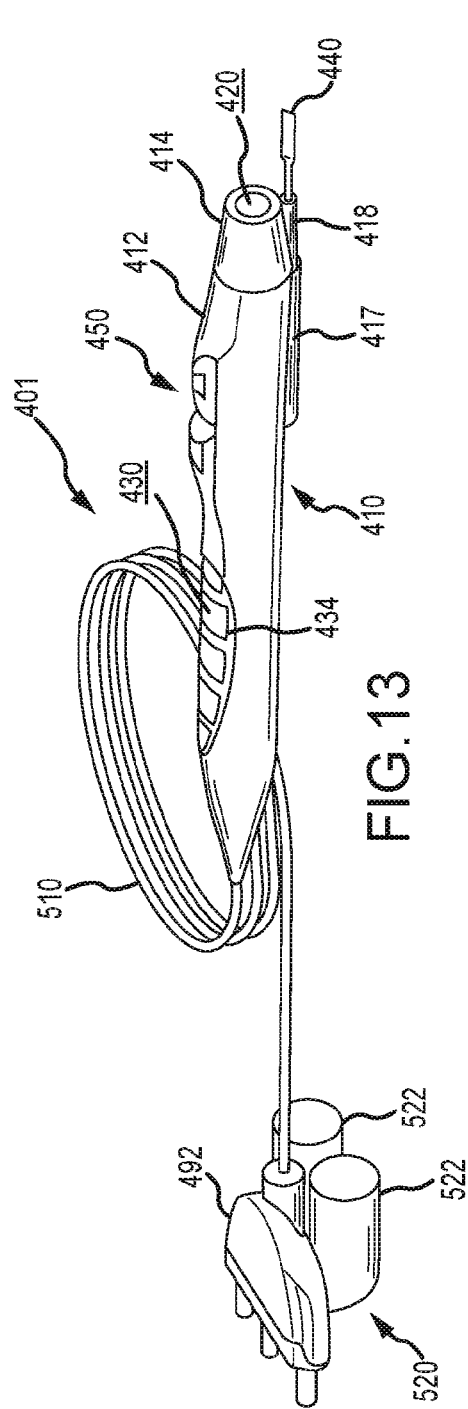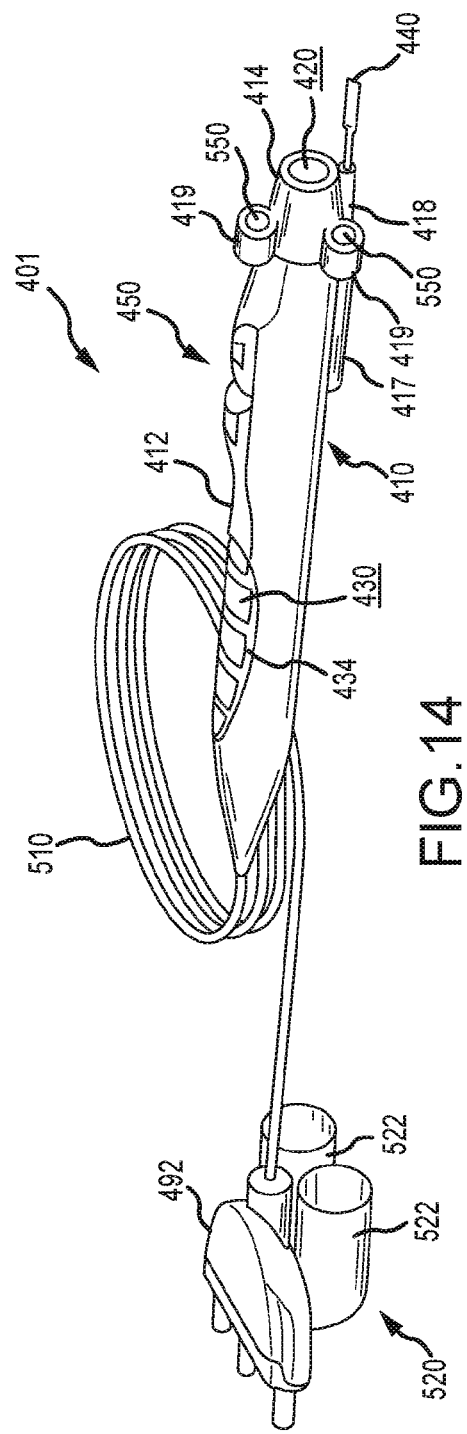

HAND-HELD ELECTROSURGICAL INSTRUMENT

RELATED APPLICATION

This application is a continuation-in-part of U.S. application Ser. No.: 13/405,923 filed on Feb. 27, 2012, entitled "HAND-HELD ELECTROSURGICAL INSTRUMENT," which claims priority to U.S. Provisional Application No.: 61/447,562 filed Feb. 28, 2011, entitled "HAND-HELD ELECTROSURGICAL INSTRUMENT." This application is also a continuation-in-part of U.S. application Ser. No. 14/561,082 filed Dec. 4, 2014, entitled "HAND-HELD SMOKE EVACUATION INSTRUMENT," which claims priority to U.S. Provisional Application No. 61/911,864 filed on Dec. 4, 2013, entitled "HAND-HELD SMOKE EVACUATION INSTRUMENT." Each of the foregoing applications are incorporated herein by reference in their entirety.

FIELD OF THE INVENTION

The present invention generally relates to surgical instruments, and more particularly to hand-held electrosurgical instruments.

BACKGROUND OF THE INVENTION

Electrosurgery is a well-known surgical approach employed to reduce tissue damage and blood loss during operating room and outpatient procedures. In electrosurgery, tissue of a patient adjacent to an electrode conductor is excited by a high frequency electric current passing from the electrode conductor to the tissue of the patient. Depending upon the characteristics of the electrical current and method employed by a user, different electrosurgical operations may be performed with the electrosurgical instrument. For instance, an electrosurgical instrument may be used to cut, coagulate (coag), desiccate, or fulgurate tissue.

As with many surgical instruments, electrosurgical instruments may require the user to accurately and precisely guide the electrosurgical instrument when performing an electrosurgical operation. In this regard, consistent pressure and stability are necessary to realize accuracy when using the electrosurgical instrument. As such, an electrosurgical instrument may be of a size such that the electrosurgical instrument may be readily gripped by the user to accurately and precisely maneuver the electrosurgical instrument. For example, many electrosurgical instruments are similar in size and shape to a writing instrument.

The high frequency electrical current used to perform various electrosurgical operations may be generated by electrosurgical equipment (e.g., an electrosurgical generator). In turn, a signal cable may extend between the electrosurgical instrument and the electrosurgical equipment to facilitate electrical communication therebetween.

In this regard, when electrosurgical instruments rest on a surface (e.g., an operating room table, the patient, etc.) the instruments may be free to roll about a longitudinal axis of the electrosurgical instrument, which may result in inadvertent activation of the electrosurgical instrument. This increases the potential for injury to the user and/or patient and may result in damage to the electrosurgical instrument.

The signal cable extending from the electrosurgical instrument to the electrosurgical equipment may have a certain amount of elastic memory. This may cause the electrosurgical instrument to roll when disposed on a support surface such that a side load on one or more of the actuators may activate the electrosurgical instrument. Furthermore, if an electrosurgical instrument is to roll off a support surface and fall, the electrosurgical instrument may be damaged as a result of the fall.

Electrosurgical instruments may also have independent actuators to activate one or more operational states. These independent actuators may require a user to reposition one or more fingers with respect to the electrosurgical instrument to control the different actuators. This may result in inconsistent pressure, create movement, and reduce the stability of the electrosurgical instrument, thus leading to reduced accuracy.

Additional devices maybe employed during an electrosurgical operation. For instance, operating room lighting may allow a user to have an improved view of the surgical field. In this regard, lighting arrays may be provided in operating rooms or outpatient clinics to assist in illuminating the surgical field. Additionally or alternatively, bulky fiber-optic cable can also be used to illuminate the surgical field by being placed in or near the surgical field. Additional light emitters, such as headlamps and the like, worn by medical personnel may also be employed. However, in all these instances the light emitter is generally provided some distance away from the electrosurgical instrument, and/or away from the surgical field. As such, the surgical instrument and light emitters are separated and shadows may be cast on the surgical field by the user, the electrosurgical instrument, or other obstructions (e.g., table drapes, other devices utilized during surgery, user's hand, etc.). In short, known light emitters may fail to provide a sufficient amount of unobstructed light at the surgical field of interest.

SUMMARY OF THE INVENTION

In view of the foregoing, a primary objective of the present invention is to provide an improved electrosurgical instrument operation and environment.

Another objective is to provide an improved electrosurgical instrument and method that may be employed to enhance medical personnel efficiencies attendant to an electrosurgical procedure.

An additional objective is to provide an improved electrosurgical instrument that is relatively simple in construction and assembly.

Another objective is to provide an improved electrosurgical instrument that is less likely to inadvertently roll and inadvertently activate when disposed on a surface.

Yet another objective is to provide an improved electrosurgical instrument that facilitates an improved environment via enhanced illumination of the surgical field of interest, e.g., by eliminating the obstruction of light cast on the surgical field of interest.

Another objective is to provide an improved electrosurgical instrument that improves the ability of a user to accurately and precisely manipulate the surgical instrument when activating an operational state of the electrosurgical instrument.

Numerous additional features and advantages of the present invention will become apparent to those skilled in the art upon consideration of the embodiment descriptions provided hereinbelow.

In one aspect, a hand-held electrosurgical instrument is provided that includes a handle portion, and an electrosurgical electrode and light emitter supportably interconnected to the handle portion. The instrument further includes a toggle member that is supportably interconnected to the handle portion. The toggle member is manipulatable to effect activation of at least one operational state of the electrosurgical instrument, (e.g., to cut, coagulate, desiccate and/or fulgurate tissue utilizing a plurality of different electrosurgical signals supplied by electrosurgical equipment) and to effect emission of light from the light emitter.

The light emitter may include at least one light source supportably interconnected to the handle portion. Additionally, a power source may be supportably interconnected to the handle portion and operatively interconnected to the light source(s). In turn, the light source(s) may be selectively activatable by manipulation of the toggle member to emit light, free from interconnection to external energy sources.

In the latter regard, the electrosurgical instrument may be free from additional wire, power cables or remote light transmitters (e.g., fiber-optic cable) running between electrosurgical equipment and the electrosurgical instrument. Accordingly, drag applied to the hand of the user due to additional wire or cable resting on the user may be reduced. The elimination of additional wire or cable may also help to prevent wrist fatigue and grip fatigue, thus improving the endurance of the user using the electrosurgical instrument.

The toggle member may be selectively manipulated to at least a first position to effect activation of a first operational state of the electrosurgical instrument and to a second position to effect activation of a second operational state of the electrosurgical instrument. Additionally, the toggle member may be biased to a home position and selectively manipulatable from the home position to the first position and to the second position by a user. When the toggle member is in the home position, the electrosurgical instrument may be in an inactive state (e.g., such that the electrosurgical electrode and light emitter are both inactive).

Further, the toggle member may be provided to be selectively manipulated to a third position to effect simultaneous activation of both the first operational state of the electrosurgical instrument and the emission of light from the light emitter. Additionally, the toggle member may be provided to be selectively positionable to a fourth position to effect simultaneous activation of both the second operational state of the electrosurgical instrument and the emission of light from the light emitter. In some arrangements, the toggle member may be manipulated to a fifth position to independently activate the light emitter, without activating the electrosurgical instrument, e.g., by vertically depressing the toggle.

The toggle member may be directly manipulatable between the home position and any of the first position, the second position, the third position, the fourth position, or the fifth position. In this regard, the toggle member may comprise a single tactile interface point which allows the user to selectively activate any operational state of the electrosurgical instrument.

As may be appreciated, various implementations may be provided in which the toggle member may be randomly manipulated to activate the light emitter prior to activation of any operational state. Additionally or alternatively, various implementations may be provided in which the toggle member may be randomly manipulated to activate any operational state prior to activation of the light emitter.

In various embodiments, the toggle member may be selectively positionable in a first position to effect activation of a first operational state of the electrosurgical instrument, and in a second position to effect only the emission of light. In this regard, at least a portion of the toggle member may be manipulatable in a first dimension relative to the handle portion to effect activation of at least one operational state of the electrosurgical instrument, wherein the toggle member may be manipulatable in a second dimension to effect the emission of light.

In some arrangements, the electrosurgical electrode may be provided to extend away from a first end of the handle portion. At least a portion of the toggle member may be at least one of advanceable towards and retractable from the first end of the handle portion to effect activation of at least one operational state. In addition, at least a portion of the toggle member may be depressible relative to the handle portion to effect the emission of light.

In another aspect, a hand-held electrosurgical instrument is provided that includes an electrosurgical electrode and an elongate handle portion. The electrosurgical electrode is supportably interconnected to and extends away from a first end of the handle portion. At least a contoured segment of the handle portion may be configured to restrict rolling of the electrosurgical instrument when disposed on a support surface. Accordingly, the electrosurgical instrument may reduce the potential for inadvertent activation of the electrosurgical instrument and reduce the potential of the electrosurgical instrument falling from the surface.

In some embodiments, the electrosurgical instrument may include a signal cable fixedly interconnected to and extending away from a second end of the handle portion (e.g., opposite to the first end of the handle portion). The signal cable may be operatively interconnected to the electrosurgical electrode to provide a signal thereto from electrosurgical equipment.

The electrosurgical instrument may also include a toggle member supportably interconnected to the handle portion that is selectively manipulatable by a user to effect activation of at least one operational state of the electrosurgical instrument. The toggle member may be located on a first side of the contoured segment of the handle portion. The contoured segment may further include at least two additional sides located directly adjacent to the first side and to each other. Accordingly, in one embodiment, the two additional sides and the first side may define a triangular configuration along the contoured segment of the handle portion.

In some arrangements, the electrosurgical instrument may include at least three light sources that are disposed about an adjoinment region between the electrosurgical electrode and the first end of the handle portion to which the electrosurgical electrode is supportably interconnected. A longitudinal axis of the handle portion and a center axis of the electrosurgical electrode may be one of aligned or parallel such that the light sources are spaced about the center axis. In turn, enhanced illumination about the electrosurgical electrode eliminates electrode shadows.

Additionally, the electrosurgical instrument may include a triangularly-configured, light transmissive nose that is interconnected to the first end of the housing and disposed about the at least three light sources. The nose may taper away from the one end of the handle portion towards the center axis of the electrosurgical electrode. The contoured segment of the handle portion and the nose may be externally configured to define a conformal transition therebetween.

In another aspect, a hand-held electrosurgical instrument may be provided that is sealed from external fluids. For instance, an elastomeric material may be provided that covers and substantially encases at least a handle portion of the electrosurgical instrument. The elastomeric material may extend continuously and uninterrupted, and may be impenetrable to fluids. The elastomeric handle portion may seal one or more internal portions of the electrosurgical instrument.

In some embodiments, a proximal seal and a distal seal may be provided at either end of the continuously-extending, elastomeric handle portion to further isolate the interior of the electrosurgical instrument from fluids (e.g., fluids that come into contact with the instrument during an electrosurgical procedure such as bodily fluids, saline, etc.). The elastomeric handle portion may also provide a gripping surface designed to facilitate a non-slip interface between a user's hand (or a glove provided thereon) and the instrument.

Furthermore, in some embodiments, the elastomeric handle portion may extend continuously with respect to a toggle member. As such, the elastomeric handle portion may be deflectable at the toggle member to allow for selective manipulation of the toggle member. The elastomeric handle portion may remain continuous over the toggle member when deflected such that the toggle member is sealed regardless of the position of the toggle member.

In an additional aspect, a hand-held electrosurgical instrument may be provided that includes a handle portion, an electrosurgical electrode that is supportably interconnected to and extends away from a first end of the handle portion in a first direction, and at least on electrically-powered component interconnected to the handle portion. The electrically-powered component may be a light emitter for emitting light in the first direction to illuminate a predetermined volume extending from the first end of the handle portion to a distal end of the electrosurgical electrode. The volume extends about a majority of the electrosurgical electrode.

The light emitter may be adapted to emit light from a plurality of locations spaced about an adjoinment region between the electrosurgical electrode and the handle portion. In some embodiments, the light emitter may include a plurality of light sources. Different ones of the plurality of light sources may be located at different ones of the plurality of locations for emitting light. For instance, the plurality of light sources may include at least three light sources disposed about an adjoinment region between the electrosurgical electrode and the handle portion. The light emitter may further include a light transmissive nose that is disposed about the at least three of light sources.

The instrument may also include a power source for providing power to the electrically-powered component(s). In particular, the power source may be operatively interconnected in series or parallel to each of the plurality of light sources. Accordingly, the plurality of light sources may be operable to emit light free from interconnection to external energy sources. The power source may include at least one power storage device, e.g., at least one battery. In one arrangement, the power source may include one or a plurality of batteries electrically interconnected in series or in parallel and supportably interconnected to the handle portion. In another arrangement, the power source may include one or a plurality of batteries (e.g., a battery pack) remotely located from the handle portion, and an electrical cable to provide electrical power from the battery or batteries to the electrically-powered components (e.g., one or more light sources).

In one aspect, the light emitters may be a light emitting diode that emits at least 1,000 millicandela (mcd) of light. In turn, the light emitter may be activatable to illuminate the entirety of the predetermined volume with at least 1,000 mcd of light. In one embodiment, different ones of the plurality of light sources may emit light at corresponding different predetermined wavelengths. Additionally, the plurality of light sources may emit light of a color temperature of at least about 3,000K.

In relation to various embodiments described herein, the term "toggle member" is used only to describe the ability to activate different operational states and/or the emission of light. In turn, no particular structure or limited number of states is implied by use of the term "toggle", unless otherwise specified. For instance, a "toggle member" may be operative to selectively activate more than two operational states. As such, the term "toggle" is not intended to limit the functionality of the "toggle" member to selection of a single state from a limited number of states. Rather, the term "toggle" is intended to more broadly define the ability to selectively activate at least one of a plurality of states without limitation to the possible number of states of the "toggle member".

Additionally, as noted, the term "toggle member" is not intended to denote any particular structure. For instance, a toggle switch may be known in the art for selection of only one of a plurality of states of the switch. As used herein, "toggle member" is intended to encompass such switches, as well as alternatives, to the extent such switches are operative in a manner corresponding to the discussion presented herein.

In an additional aspect, a method for operating a hand-held electrical instrument to conduct electrosurgery is provided. The method includes a step of manipulating a toggle member comprising the hand-held electrosurgical instrument to effect activation of at least one operational state of the electrosurgical instrument, (e.g., to cut, coagulate, desiccate and/or fulgurate tissue utilizing a plurality of different electrosurgical signals supplied by electrosurgical equipment), and to effect emission of light from a light emitter comprising the electrosurgical instrument.

In various arrangements, the method may further include the steps of establishing a single tactile interface between a finger of a user and the toggle member of the electrosurgical instrument, and maintaining the single tactile interface throughout the manipulating step (e.g., to both effect activation of at least one operational state of the electrosurgical instrument and to effect emission of light from the light emitter). Again, the ability to maintain a single tactile interface with a toggle member, while controlling operation of an electrosurgical instrument, advantageously yields enhanced precision.

In various arrangements the manipulating step of the method may further comprise the steps of positioning the toggle member in the first position to effect activation of a first operational state of the electrosurgical instrument and/or positioning the toggle member in a second position (e.g., different than the first position) to effect activation of a second operational state of the electrosurgical instrument. Further, the method may optionally include a step of biasing the toggle member to a home position that is different than the first position and the second position, wherein the toggle member is selectively positionable from the home position to the first position and to the second position by a user, and wherein the electrosurgical instrument is in an inactive state when the toggle member is in the home position.

In at least one embodiment, the manipulating step of the method may further include positioning the toggle member in a third position (e.g., different than the first and second positions) to effect simultaneous activation of a first operational state of the electrosurgical instrument and the emission of light from the light emitter. Further, the manipulating step may optionally include the step of positioning the toggle member in a fourth position (e.g., different than the first, second and third positions) to effect simultaneous activation of a second operational state of the electrosurgical instrument and the emission of light from the light emitter.

In relation to the noted potential method steps, the toggle may be provided to be directly positionable between a home position and any one of the first position, the second position, the third position and/or the fourth position. In this regard, enhanced control and functional efficiencies may be realized.

In one arrangement, the electrosurgical instrument may include an electrosurgical electrode supportably interconnected to and extending from a first end of a handle portion of the electrosurgical instrument, wherein the manipulating step may further include one of either advancing the toggle member towards or retracting the toggle member away from the first end of the handle portion of the electrosurgical instrument to effect activation of the at least one operational state of the electrosurgical instrument. Further, the manipulating step may also include depressing the toggle member relative to the handle portion to effect the emission of light.

In various embodiments, the method may further include the step of illuminating a majority of a volume extending from a first end of a handle portion of the electrosurgical instrument in a direction towards a distal end of an electrosurgical electrode supportably interconnected to and extending away from the first end of the handle portion. In this regard, illumination may be realized in the volume at predetermined light levels consistent with those noted hereinabove.

In some implementations, the illuminating step may comprise emitting light from a plurality of locations at the first end of the handle portion of the electrosurgical instrument in a direction towards the distal end of the electrosurgical electrode. In some implementations, the emitting step may comprise powering a plurality of light sources, each of the plurality of light sources being disposed at different ones of the plurality of locations.

In one approach, powering of the light sources may comprise supplying an electrical signal from at least one power storage device comprising the electrosurgical instrument (e.g., one or more batteries). As may be appreciated, such electrical signal supply may be provided and controlled in conjunction with the manipulating step.

In another aspect, a hand-held instrument is provided for smoke evacuation. The instrument may be conveniently utilized in connection with a medical procedure in which electrical or another form of energy is applied to a tissue site, thereby resulting in the generation of smoke.

In one embodiment, a hand-held instrument includes a housing sized for hand-held use and defining at least a portion of an internal volume of the hand-held instrument. The instrument may further include an inlet port and an outlet port for gas passage into and out of the internal volume. An impeller may be disposed within the internal volume between the inlet port and the outlet port. To rotate the impeller, a motor may be disposed within the internal volume, wherein upon powered rotation of the impeller by the motor, gas flow into the inlet port and out of the outlet port may be induced. For example, an internal gas flow rate of at least 3.0 ft.$^3$/min. may be provided. As may be appreciated, the provision of a hand-held instrument having on-board componentry for powered smoke evacuation through the instrument yields an effective and efficient solution to one or more of the problems noted hereinabove, and is particularly apt for extracorporeal use.

In some implementations, the hand-held instrument may comprise a filter located at the outlet port for filtering smoke-laden gas flowing in to the inlet port and out of the outlet port. The filter may be provided for capture of particles, e.g., particles having a minimum size, or cross-dimension, of 0.12 microns or larger. Further, the filter may provide for adsorption and/or absorption of undesirable gas smoke constituents, e.g., cytotoxins, papillomavirus, mutagens. Optionally, the filter may include a filter element that is readily replaceable.

In some embodiments, the hand-held instrument may be provided so that the inlet port is located at or proximate to a distal end of the hand-held instrument, and wherein the outlet port is located proximal to the impeller. To provide for enhanced gas flow from the impeller to the outlet port, the hand-held instrument may include a gas flow member located proximal to the impeller within the internal volume between the impeller and the outlet port. The gas flow member may comprise a plurality of blades extending in a direction parallel to a desired gas flow path so as to direct the gas flow from the impeller to the outlet port.

In one approach, the outlet port may be disposed along a side of the housing of the hand-held instrument. For example, the outlet port may be located along an elongate side portion of the housing so as to direct gas flow from the outlet port laterally away from the hand-held instrument. In some embodiments, the hand-held instrument may further include an internal side wall that defines a portion of the internal volume proximal to the impeller, wherein a portion of the side wall is angled (e.g., curved) across a longitudinal axis of the hand-held instrument to the outlet port so as to direct gas flow from the impeller to the outlet port.

In certain embodiments, the housing of the hand-held instrument may include a first member that includes the outlet port, and a second member that includes the inlet port. The first member and the second member may be interconnected and otherwise disposed for relative movement therebetween. For example, the first and second members may be disposed for relative movement therebetween along a longitudinal axis of the hand-held instrument, wherein the second member is positionable in at least a retracted first position and an extended second position distal to the first position. In contemplated approaches, the second member may be selectively positionable by a user relative to the first member at a continuum of positions along the longitudinal axis. For such purposes, the first and second members may be slidably interconnected along the longitudinal axis. In that regard, a proximal end portion of the second member may be provided so as to extend into a distal end portion of the first member for telescoping movement relative thereto. In such embodiments, the first member and second member may each be of a tubular configuration.

In some implementations, the hand-held instrument may also include at least one light emitter for emitting light in a direction distal to a distal end of the housing. For example, in embodiments in which the housing includes a first member and a second member, as described above, the light emitter(s) may be supportably interconnected to and outside of the second member for emitting light in a direction distal to a distal end of the second member. In some implementations, a plurality of light emitters may be supportably interconnected to the housing. For example, at least three light emitters may be interconnected in spaced relation about the housing.

In some embodiments, at least one hand switch may be included in the hand-held instrument for operational control of the motor. For example, the hand switch may be provided for selectively turning the motor on and off, and in some implementations to control the speed of the motor output and resulting impeller rotation and attendant gas flow rate. In some implementations, the hand switch(es) may be conveniently located along a side of the housing, wherein a user may grasp/manipulate the hand-held instrument with a given hand so as to orient the inlet port where desired for smoke intake, and also utilize the same hand to operate the hand switch. Where the housing comprises first and second members, as discussed above, the hand switches may be conveniently located on the proximal first member, distal to the outlet port.

In some implementations, the motor may be disposed proximal to the impeller and the outlet port. Such positioning facilitates the maintenance of an open internal volume between the inlet port and the outlet port so as to optimize gas flow therebetween. Further, such positioning facilitates interconnection of the motor with a power source. In one approach, the hand-held instrument may comprise at least one battery for electrically powering the motor, wherein both the motor and the battery may be disposed within the internal volume proximal to the impeller and the outlet port. In some implementations, the one or more batteries may be replaceable. In another approach, the electrosurgical instrument may be provided with or interconnectable to electrical cabling at a proximal end, wherein the electrical cabling may be electrically interconnected or interconnectable to the motor. The electrical cabling may extend proximally away from the housing to a proximal end that may be electrically interconnectable to an appropriate electrical power source (e.g., via a plug-in coupler end), or that may be electrically interconnected to one or a plurality of batteries located in a battery module. In the later regard, a battery module may be provided along the electrical cabling for supporting at least one removable/replaceable battery in electrical contact with the electrical cabling at a location that is advantageously spaced from the housing and components housed therein.

In an embodiment, a hand-held instrument may include a housing sized for hand-held use that defines at least a portion of an internal volume of a hand-held instrument, an inlet port and an outlet port for gas passage into and out of the internal volume, and an impeller disposed within the internal volume between the inlet port and the outlet port. Additionally, an energy emission component may be integrated for energy application to a tissue site. In contemplated approaches, the energy emission component may be supportably connected to and extend distally from the hand-held instrument at a distal end of the housing. Advantageously, the energy emission component may be disposed in parallel or aligned relation to a longitudinal axis (e.g., a center axis) of the housing at the distal end thereof. The energy emission component may comprise an electrosurgical electrode, a laser beam emitter, or another component for conveying energy to a tissue site to achieve a desired effect (e.g., to cut and/or coagulate tissue).

In one arrangement, the hand-held instrument may further include at least one light emitter supportably interconnected to the housing for emitting light in a direction distal to a distal end of the housing, e.g. so as to illuminate a volume that includes all or at least a distal end portion of the energy emission component (e.g. electrosurgical electrode) and/or tissue site. For example, a plurality of light emitters (e.g. light emitting diodes) may be provided in spaced relation about the housing (e.g. in a ring-shaped arrangement at a common location along a center axis of the housing), wherein the light emitters may illuminate a volume that includes at least a distal end portion of an electrosurgical electrode and/or a tissue site.

In contemplated embodiments in which the housing comprises a first member and a second member as described above, an energy emission component (e.g., an electrosurgical electrode) may be supportably interconnected to and extend distally away from the distal end of the second member for co-movement therewith. In turn, a user may selectively position the second member and interconnected energy emission component at a desired position relative to the first member via selective sliding movement of the second member relative to the first member. For example, the first and second members may be slidably interconnected as described above so that the second member may be selectively positioned by a user at a continuum of positions along a longitudinal axis of the hand-held instrument. In such embodiments that integrate an electrosurgical electrode, the electrode may be disposed in parallel or aligned relation to the longitudinal axis. Further, the instrument may include a first electrical contact (e.g., an elongate metal strip) mounted to the first member (e.g., parallel to a longitudinal axis of the instrument) and a second electrical contact (e.g., a metal strip) mounted to the second member so that the second electrical contact is maintained in slidable contact engagement with the first electrical contact when the second member is selectively positioned by a user at any of the continuum of positions.

In some embodiments the hand-held instrument may include cabling interconnected to an integrated energy emission component and extending proximally from the housing, wherein the cabling may be interconnected to a source for providing an energy signal to the energy emission component. For example, electrical cabling may be provided for electrical interconnection to an electrosurgical generator, wherein the electrosurgical generator may provide an electrosurgical tissue cutting signal and/or an electrosurgical tissue coagulation signal to an integrated electrosurgical electrode comprising the hand-held instrument upon user manipulation of one or more control switches provided on the housing of the hand-held instrument.

In various embodiments, a motor may be included in the integrated hand-held instrument, as described above. Further, the hand-held instrument may include an onboard power source (e.g., one or more batteries that may be replaceable) or electrical cabling electrically interconnectable to an appropriate source for powering operation of the motor for smoke evacuation at a tissue site. In one approach, electrical cabling may be interconnected to the motor and routed together with electrical cabling for interconnection to an electrosurgical generator, wherein a proximal coupler end may comprise one or more batteries (e.g., replaceable DC batteries) for powering the motor.

In conjunction with a hand-held instrument for smoke evacuation, an inventive method is also provided. In one embodiment, the method may include the steps of utilizing a motor of a hand-held instrument to induce gas flow into an inlet port and out of an outlet port of a hand-held instrument, and positioning the hand-held instrument so as to locate the inlet port of the hand-held instrument proximate to a smoke source (e.g., a patient tissue site), wherein smoke-laden gas is drawn into the inlet port of and evacuated through the outlet port of the hand-held instrument. The method may further include a step of filtering the gas flow, e.g., by interconnecting a filter member to the hand-held instrument at the outlet port. In some embodiments, the method may further provide for directing the gas flow laterally away from the hand-held instrument through the outlet port thereof.

In certain implementations, the motor utilization step may include controlling the initialization and/or termination of operation of the motor via manipulation of at least one hand switch of the hand-held instrument. Such motor control may be achieved by the same user hand that is also employed for positioning the hand-held instrument.

The method may further include the step of directing gas flow through at least a portion of the internal volume of the hand-held instrument along the longitudinal axis of the hand-held instrument. By way of example, a gas flow member may be disposed within an internal volume of the hand-held instrument between an impeller and the outlet port to direct the gas flow therebetween.

In some embodiments, the method may further include the step of supplying a signal to an energy emission component of the hand-held instrument. As noted, the energy emission component may comprise an electrosurgical electrode, wherein an electrical signal may be supplied for tissue cutting and/or tissue coagulation. When employed, an energy emission component may be supportably interconnected to and extend distally from a distal end of a housing of the hand-held instrument. In that regard, the housing may include a first member that includes the outlet port and a second member that includes the inlet port, wherein the first member and second member are slidably interconnected and disposed for relative movement therebetween. In such arrangements, the energy emission component may be supportably connected to the second member for co-movement therewith wherein the method may further include the step of locating the energy emission component by slidably positioning the second member relative to the first member.

In embodiments employing an energy emission component, the energy emission component may be employed to deliver energy to a patient tissue site in conjunction with a medical procedure. In turn, such application of energy may result in the generation of smoke at the patient tissue site. As may be appreciated, in such embodiments the method provides for the convenient single-hand positioning and use of a single hand-held instrument for both the application of energy to a patient tissue site and for the removal of smoke generated in connection with the energy application.

Various additional method implementations and options may be realized utilizing different ones of the features noted above in relation to embodiments of an improved hand-held electrosurgical instrument. Still further features of an improved electrosurgical instrument and related method will be appreciated upon consideration of the embodiment descriptions provided hereinbelow.

BRIEF DESCRIPTION OF THE DRAWINGS

FIG. 1D is a bottom view of the embodiment of FIG. 1A.
FIG. 9A is a top view of another hand-held instrument embodiment.
FIG. 9B is a side view of the hand-held instrument embodiment of FIG. 9A.
FIG. 9C is a bottom view of the hand-held instrument embodiment of FIG. 9A.
FIG. 9D is a distal end view of the hand-held instrument embodiment of FIG. 9A.
FIG. 10A is a cross-sectional side view of the hand-held instrument embodiment of FIG. 9A taken along section line A-A of FIG. 9A.
FIG. 10B is a cross-sectional top view of the hand-held instrument embodiment of FIG. 9A taken along section line B-B of FIG. 9B.
FIG. 13 is a perspective view of a modified version of the hand-held instrument embodiment of FIG. 12.
FIG. 14 is a perspective view of the hand-held instrument embodiment of FIG. 13, supplemented to include light emitters.

DETAILED DESCRIPTION

Figure 1A:
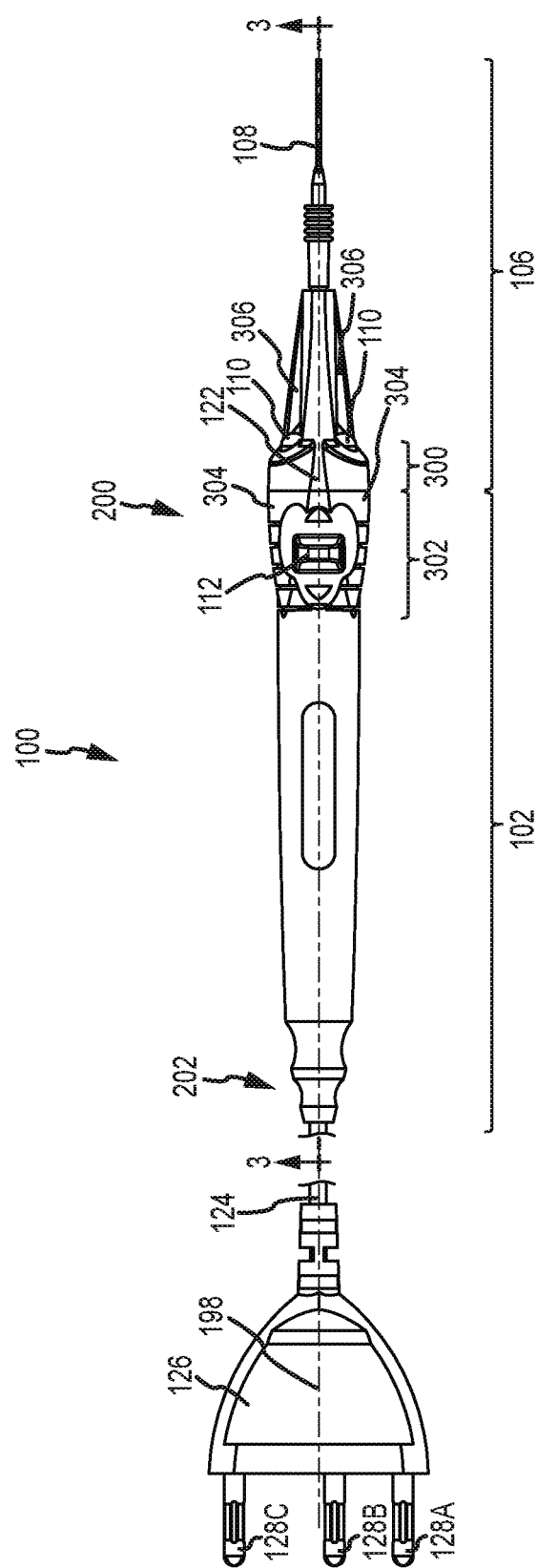
FIG. 1A is a top view of an embodiment of an electrosurgical instrument.
Figure 1B:
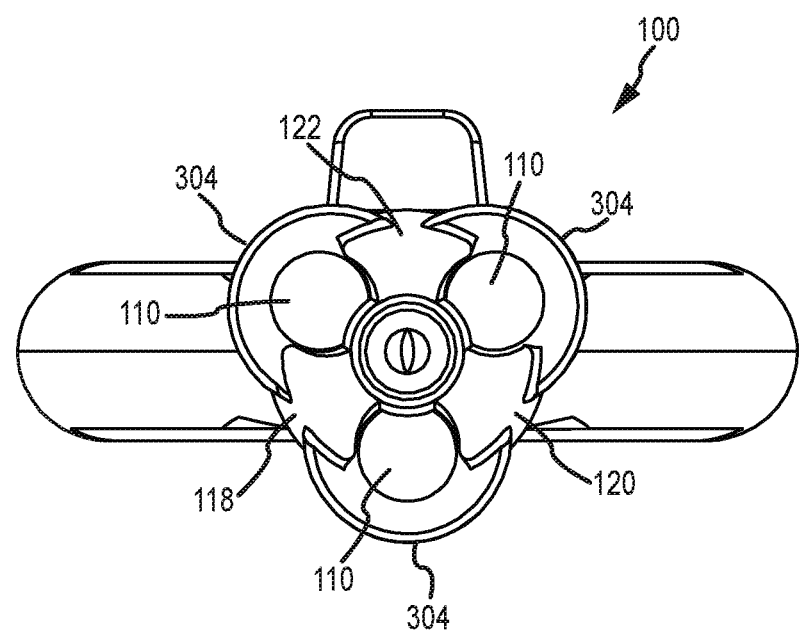
FIG. 1B is a front view of the embodiment of FIG. 1A.
Figure 1C:
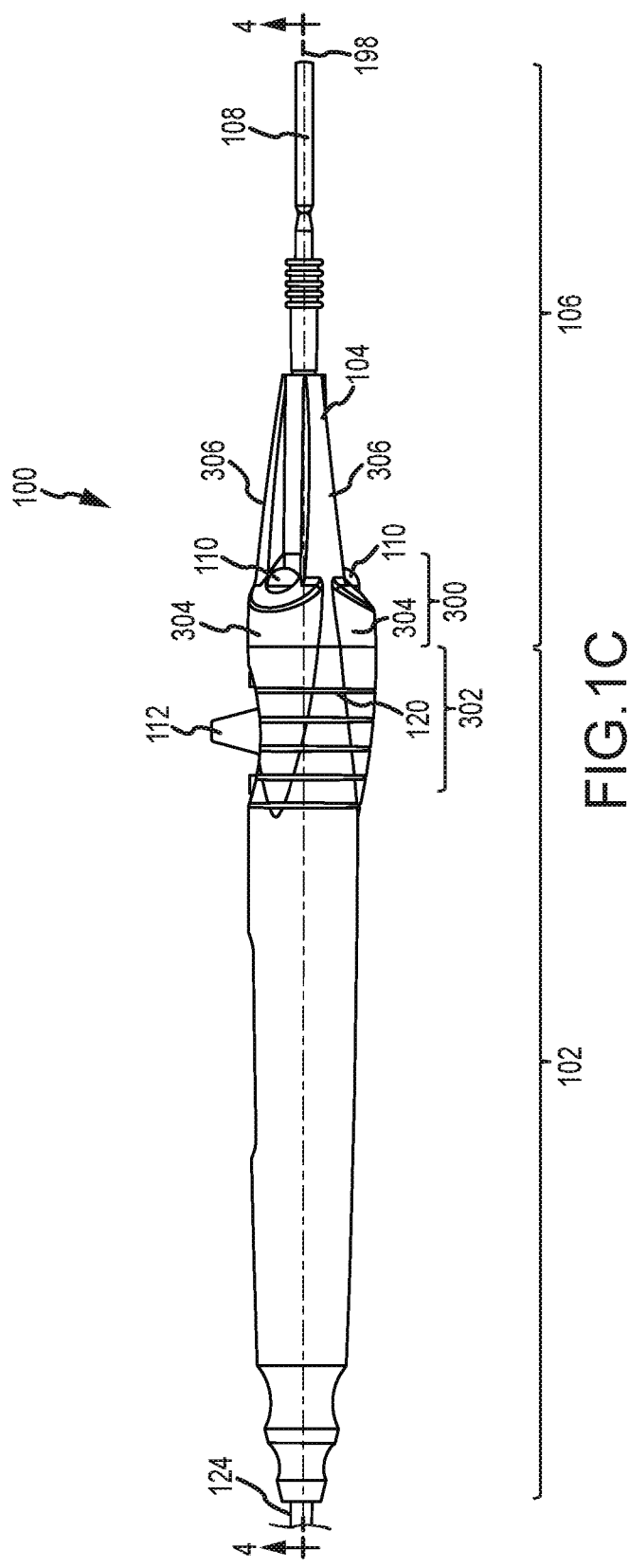
FIG. 1C is a side view of the embodiment of FIG. 1A.

The present invention may be implemented in configurations and alternative forms. Specific embodiments are presented herein by way of example. It should be understood that such embodiments are not intended to limit the invention to the particular form disclosed.

FIGS. 1A-1D depict various views of an embodiment of a hand-held electrosurgical instrument 100. The electrosurgical instrument 100 may include a handle portion 102. An electrosurgical electrode 106 may extend distally from a distal end 200 of the handle portion 102. Also, at least one light emitter(s) 300 may be disposed adjacent to a distal end 200 of the handle portion 102. The light emitter(s) 300 may be operative to emit light from at least one corresponding light emission location in a direction distally with respect to the handle portion 102. The light emitter(s) 300 and the electrosurgical electrode 106 may be supportably interconnected to the handle portion 102.

The handle portion 102 may comprise an elongate member extending along a longitudinal axis 198. The handle portion 102 may have a distal end 200, as referenced above, and a proximal end 202. The distal end 200 of the handle portion 102 may include a contoured segment 302. The contoured segment 302 may be configured to restrict rolling of the electrosurgical instrument 100 about the longitudinal axis 198 when resting on a support surface (e.g., an operating room table, the patient, etc.).

For instance, moment forces may be imparted on the electrosurgical instrument 100 that may cause the electrosurgical instrument 100 to roll about the longitudinal axis 198 when resting on a support surface. For a substantially cylindrical electrosurgical instrument, this may result in the generally cylindrical electrosurgical instrument rolling to an undesirable location, the electrosurgical instrument falling from the surface, or a control surface of the electrosurgical instrument contacting the support surface such that the electrosurgical instrument is inadvertently activated.

The contoured segment 302 of the electrosurgical instrument 100 may have at least one substantially flattened side (e.g., defined by at least two spaced peripheral regions extending along the configured segment and disposed in a common tangent plane) that may allow the electrosurgical instrument 100 to come to rest on that substantially flattened side and resist moment forces imparted onto the electrosurgical instrument 100.

For example, the embodiment depicted in FIGS. 1A-1D includes a first side 118, a second side 120, and a third side 122 arranged in a generally triangular configuration and extending along the contoured segment 302 of the distal end 200 of the handle portion 102. The first side 116, the second side 118, and the third side 122 may be defined as substantially flattened surfaces extending between two corresponding surface projections 304. Each of the surface projections 304 may generally comprise a conical, elliptical, or parabolic projection which tapers proximally along the length surface projection 304 as shown in FIGS. 1A-1D. In this regard, the surface projections 304 of the illustrated embodiment may taper toward the longitudinal axis 198 of the handle portion 102 in a proximal direction as shown.

In any regard, adjacent pairs of surface projections 304 may define corresponding ones of the first side 118, second side 120, or third side 122, therebetween. The first side 118 and the second side 120 may be disposed directly adjacent to each other and may intersect at a vertex corresponding to one of the surface projections 304. The third side 122 may be provided adjacent to both the first side 118 and second side 120 and intersect the first side 118 and the second side 120 at respective vertices adjacent to corresponding surface projections 304. In this regard, the generally triangular configuration of the contoured portion 302 may be operative to resist a moment force acting on the electrosurgical instrument 100, thus reducing the likelihood that the electrosurgical instrument 100 will roll about the longitudinal axis 198.

In the particular embodiment depicted in FIGS. 1A-1D, the triangular shape defined by the first side 118, second side 120, and third side 122, may help prevent the electrosurgical instrument 100 from rolling in excess of 60 degrees regardless of how in the electrosurgical instrument 100 comes to rest on a support surface. For example, in the case were the vertex of the first and second side 118 and 120 contacts a surface, the instrument may only roll at most 60 degrees in either direction prior to coming to rest on one of the first or second side 118 or 120. Accordingly the likelihood of adverse outcomes associated with a rolling electrosurgical instrument may be reduced.

Additionally, the first side 118, second side 120, and third side 122 may coordinate to define one or more control surfaces. For instance, in the depicted embodiment, a corresponding one of a user's fingers may come to rest on a respective one of the sides. In this regard, the contoured segment 302, in addition to assisting in preventing rolling of the electrosurgical instrument 100, may also provide an ergonomically shaped control surface to coordinate with a user's fingers. As such, control over the electrosurgical instrument 100 may be improved.

As briefly described above, the light emitter(s) 300 may be disposed adjacent to the distal end 200 of the handle potion 102. For instance, the light emitter(s) 300 may be supportably interconnected to the distal end 200 of the handle portion 102. The light emitter(s) 300 may be operative to emit light from one or more corresponding light emission locations in a direction distal to the distal end 200 of the handle portion 102. For example, the light emission locations may be spaced about the periphery of the handle portion 102 at the distal end 200 thereof. The plurality of light emission locations may correspond with (e.g., be aligned with) the surface projections 304 which define the respective sides of the electrosurgical instrument 100 along the contoured segment 302. In this regard, the light emission locations of the light emitter 300 may be disposed adjacent to one or more of the vertices of two adjacent sides defined by a corresponding surface projection 304.

The light emitter(s) 300 may comprise at least one light source or a plurality of light sources. For example, a plurality of light sources may be supportably interconnected to the handle portion 102 adjacent to each respective one of the plurality of light emission locations. In one embodiment, the light sources may include one or more light emitting diode (LED).

In the embodiment depicted in FIGS. 1A-1D, the light emitter(s) 300 may be defined by a plurality of LED light sources 110 disposed adjacent to the distal end 200 of the handle portion 102. The light sources 110 may be disposed so as to emit light in a direction distal to the handle portion 102.

Figure 2:
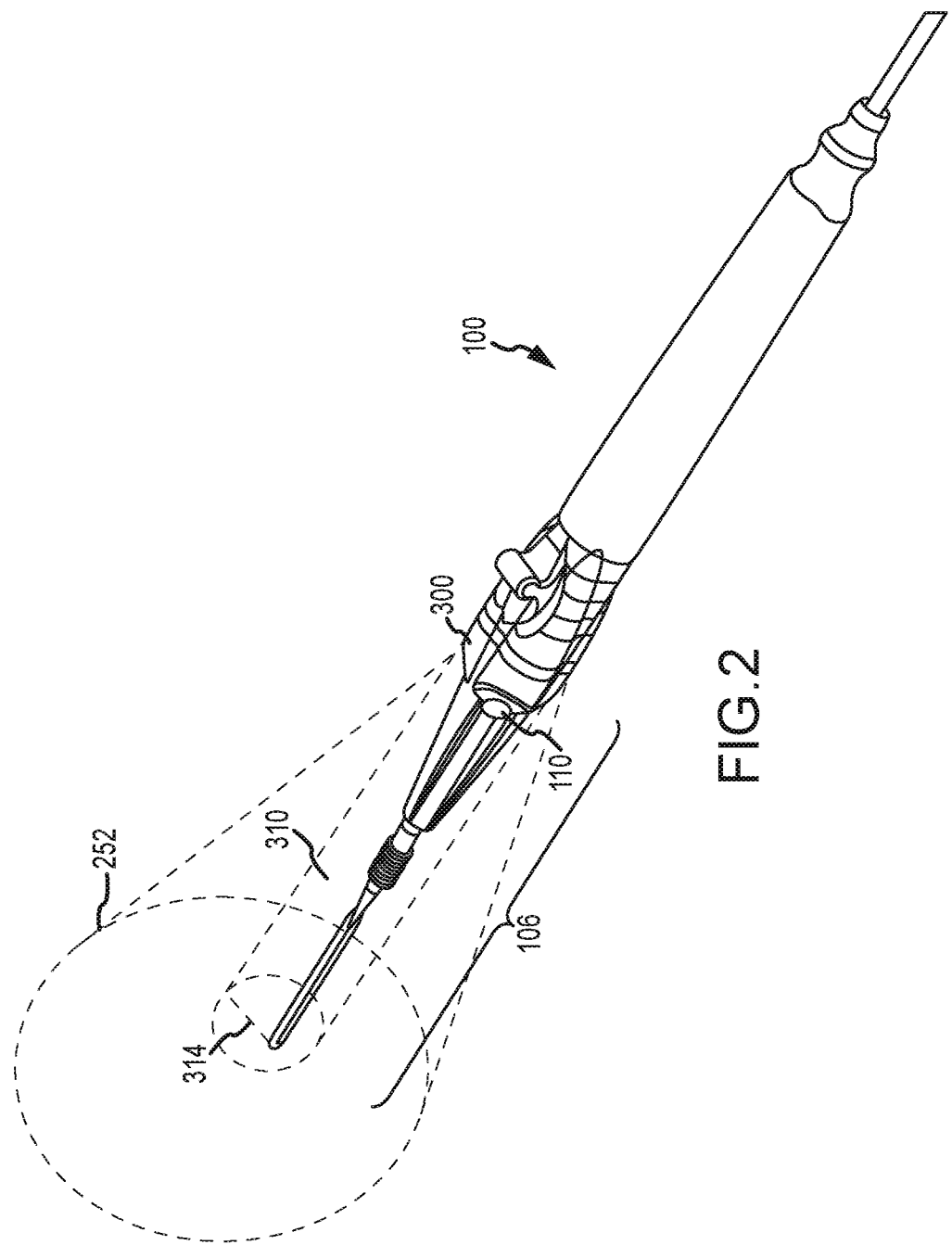
FIG. 2 is a perspective view of an embodiment of an electrosurgical instrument showing potential illumination fields of a light emitter of the electrosurgical instrument.

Wth reference to FIG. 2, at least a portion of the light emitted distally from the light sources 110 may illuminate at least a portion of a volume 252 extending distally from the light sources 110 with respect to the handle portion 102 along the length of an electrosurgical electrode 106. As shown, the volume 252 may be of a generally conical or frustoconical shape extending from the light emitter(s) 300 distally with respect to the handle portion 102.

Since the volume 252 may at least partially surround the electrosurgical electrode 106, light emitted from the light sources 110 may advantageously illuminate a relatively large surgical field of interest adjacent to where the electrosurgical electrode 106 interfaces with a patient. While one particular shape of the volume 252 is depicted, it will be understood that the shape and size of the volume 252 may be varied. For instance, light sources 110 having different light emission properties (e.g., varying power consumption, light intensities, emission angles, etc.) may be used to vary the shape and size of the volume 252 extending distally from the light emitter 300. In any regard, as the light sources 110 are generally provided distally on the handle portion 102 of the electrosurgical instrument 100, light emitted from the light sources 110 may be cast onto the surgical field of interest such that the appearance of shadows on the surgical field is reduced.

In one embodiment, the light sources 110 may illuminate at least a majority of the volume 252 with at least 1000 millicandela (mcd) of light. In another embodiment, adding additional light sources 110 may illuminate at least a majority of the volume 252 with at least 2000 mcd of light, at least 3000 mcd of light or even at least 5000 mcd of light. Each one of the light sources 110 may emit light the same wavelength or at corresponding different predetermined wavelengths. In one embodiment, the light sources 110 may emit light of a color temperature approximating incandescent or greater. For instance, the color temperature may be about 3000 K or greater.

The electrosurgical instrument 100 may also include a power source, e.g., one or more power storage device(s)

such as one or a plurality of batteries. The power source may be in selective electrical communication with the light emitter(s) 300. In that regard, electrical communication between the power source and the light emitter(s) 300 may be controlled to selectively activate the light emitter(s) 300 so as to emit light from the light emission locations distally with respect to the handle portion 102.

Figure 3:
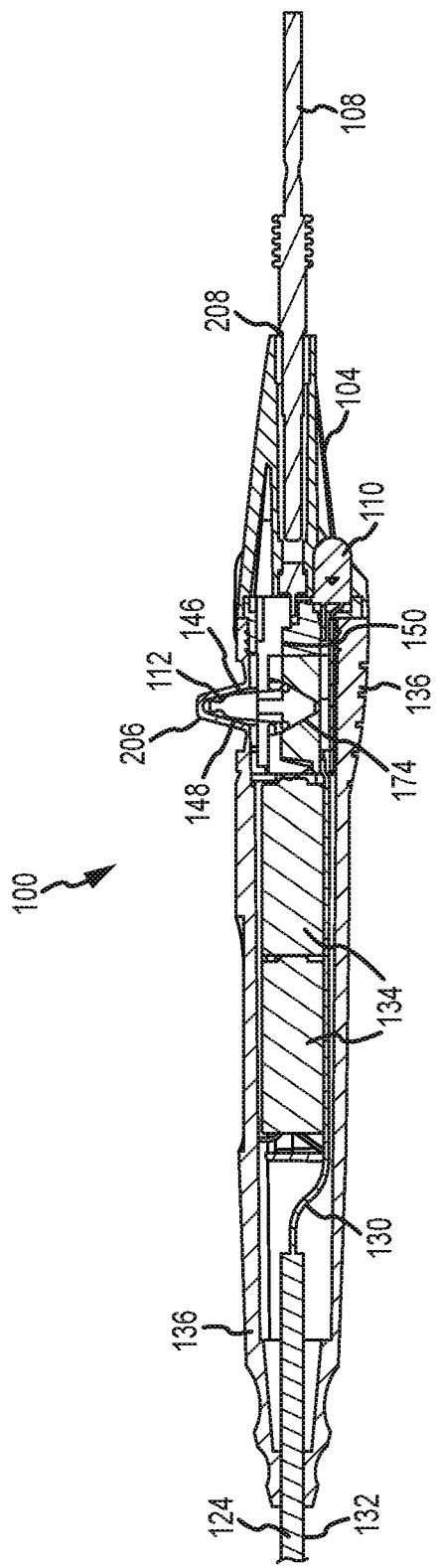
FIG. 3 is a cross sectional view of the embodiment shown in FIG. 1A taken along section line 3-3 in FIG. 1A.
Figure 4:
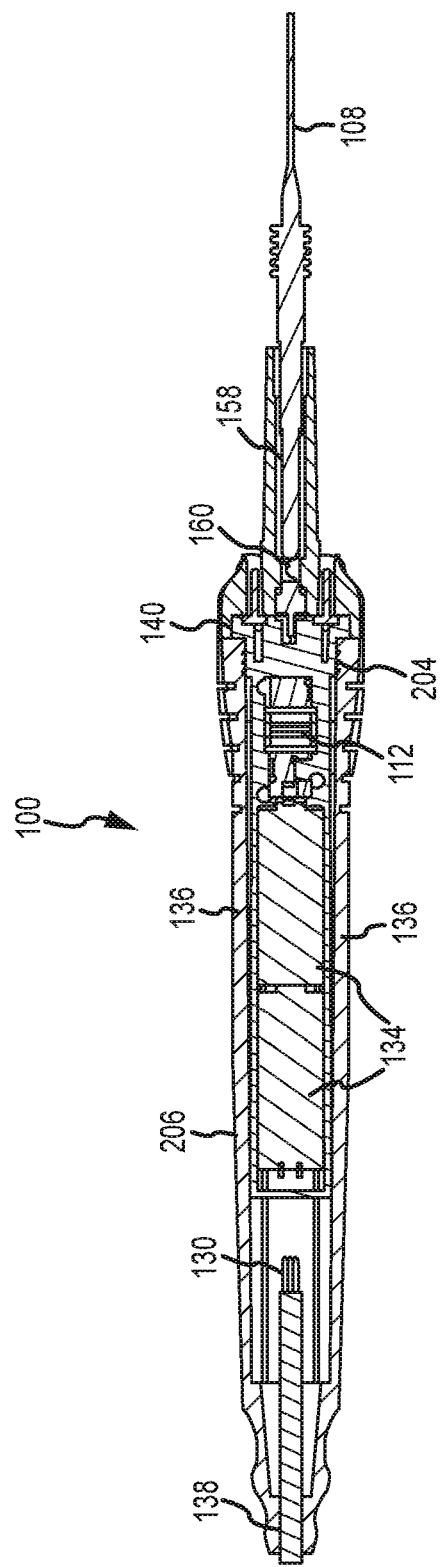
FIG. 4 is a cross sectional view of the embodiment shown in FIG. 10 taken along section line 4-4 in FIG. 10.

As shown in FIGS. 3 and 4, the power source may include one or more batteries 134 (e.g., two batteries 134 provided in a series or parallel arrangement). In this regard, at least a portion of a lighting circuit, as discussed in greater detail below, may be supportably connected to the handle portion 102 to selectively activate the light emitter(s) 300 to emit light from the light emission locations.

Alternatively, a power source may be disposed remotely from the handle portion 102 to provide power to the light emitter(s) 300, which, as described above, may be provided with the handle portion 102 or also disposed remotely from the handle portion 102. For instance, the power source may be an external battery pack located remotely from the handle portion 102, or power may be delivered via cable from the electrosurgical generator. The power source may thus be in electrical communication with the electrosurgical instrument 100, for example, by way of a wire or additional cable (e.g., extending within an existing signal cable 124).

As noted above, the electrosurgical instrument 100 may include an electrosurgical electrode 106 extending distally from a distal end 200 of the handle portion 102. The electrosurgical electrode 106 may have a bipolar configuration, a monopolar configuration, a sesquipolar configuration, or may be any other appropriate type of electrosurgical electrode 106. The electrosurgical electrode 106 may include a metallic electrode conductor 108 of any appropriate type. The electrosurgical electrode 106 may be in operative communication with electrosurgical equipment (e.g., an electrosurgical generator) (not shown in FIGS. 1A-1D) such that the electrosurgical equipment may be operable provide an electrosurgical signal to the electrode conductor 108 of the electrosurgical electrode 106. In this regard, at least one operational state of the electrosurgical instrument 100 may be activated to perform an electrosurgical operation using the electrosurgical instrument 100.

At least a portion of the electrode conductor 108 may be in selective electrical communication with one or more electrosurgical paths 130, which are in electrical communication with the electrosurgical equipment. For instance, in the embodiment depicted in FIGS. 3 and 4, the electrode conductor 108 may be retained in an electrode socket 158. The electrode socket 158 may be supportably interconnected to the handle portion 102. The electrode socket 158 is conductive which establishes electrical communication between the electrode conductor 108 and a selected electrosurgical path 130 as will be discussed in greater detail below.

Additionally, the electrode conductor 108 may be removably disposed with respect to the electrode socket 158. Accordingly, the electrode conductor 108 may be removed from the electrode socket 158 and replaced with one or more alternate electrode conductors. As such, different styles of electrode conductors 108 (e.g., blades, paddles, needles, snares, etc.) may be interchangeably fitted into the electrode socket 158. Additionally, the electrode conductor 108 may be rotated in the electrode socket 158. As such, the electrode conductor 108 may be positioned and retained by friction at different angular positions with respect to the electrode socket 158.

In the illustrated embodiment in FIGS. 1A-1D, a signal cable 124 may extend proximally from the proximal end 202 of the handle portion 102. The signal cable 124 may terminate in a plug body 126. The plug body 126 may include plurality of connectors 128A, 128B, and 128C, which extend from the plug body 126. The plug body 126 and connectors 128A-128C may be configured so as to establish electrical communication between corresponding electrosurgical paths 130 and the electrosurgical equipment (e.g., electrosurgical paths 130A-130C described below in relation to FIG. 5). In this regard, the shape and arrangement of the plug body 126 and connectors 128A-128C may correspond to an appropriate receiver on the electrosurgical equipment. That is, the shape and arrangement of the plug body 126 and connectors 128A, 128B, and 128C may comprise a standard electrosurgical connection or a proprietary electrosurgical connection corresponding to a particular type of electrosurgical equipment.

The electrosurgical instrument 100 may further include a toggle member 112. The toggle member 112 may be operative to control various aspects of the electrosurgical instrument 100. For instance, the toggle member 112 may be operative to selectively control light emission from the light emitter(s) 300. Additionally, and/or alternatively, an operational state of the electrosurgical instrument 100 may be selectively controllable by the toggle member 112. Accordingly, the toggle member 112 may be manipulated to different positions to selectively activate different operational states of the electrosurgical instrument 100 and/or control emission of light from the light emitter 300. In alternative embodiments, the toggle member 112 may include a foot switch to control the operational states of the electrosurgical instrument. In such embodiments, a finger toggle may still be provided with the electrosurgical instrument 100 to control the selectively emission of light therefrom.

In one embodiment, the toggle member 112 may present a single tactile interface point that is manipulatable by a user (e.g., a surgeon) to control the operational state of the electrosurgical instrument 100 as well as to control the emission of light from the light emitter 300. In contrast, many electrosurgical instruments include separate interface points disposed at different locations on the electrosurgical instrument for control of the activation of individual features of the electrosurgical instrument. For example, to utilize such instruments, a user must remove his or her finger from a first button, shift the position of the finger with respect to the electrosurgical instrument, and replace the finger on the electrosurgical instrument to activate the other of the buttons to activate a different state of the electrosurgical instrument. The removal and repositioning of the user's finger may result in inconsistent pressure and may reduce the ability to control the electrosurgical instrument during the time the finger is removed from the instrument. Additionally, shifting a finger with respect to the electrosurgical instrument may cause the instrument to pitch in an undesired direction. Consequently, the accuracy of the user's movements may be diminished as a neuro-surgery.

In the electrosurgical instrument 100, the toggle member 112 allows for constant contact with a single tactile interface point while selectively changing the operational state of the electrosurgical instrument 100 and/or the emission of light. In turn, activation of the various features of the electrosurgical instrument 100 does not require the user to remove his or her finger from the electrosurgical instrument 100. As a result, control of the instrument may be maintained, undesired pitching of the instrument associated with the shifting of the location of the user's finger with respect to the instrument may be avoided, and consistent pressure may be applied. In turn, the accuracy of the user's movements may be maintained even when changing between operational states of the electrosurgical instrument 100.

Figure 5:
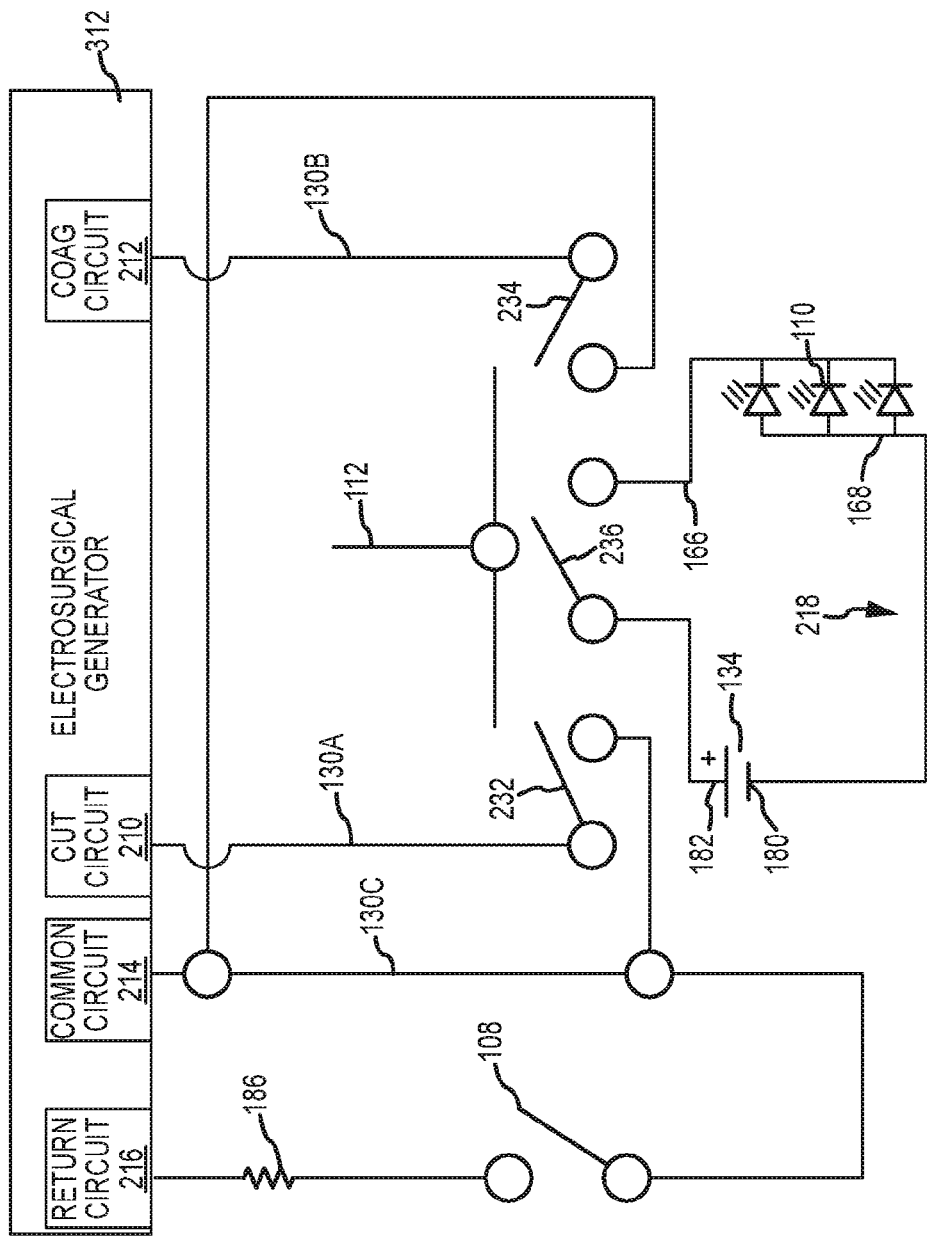
FIG. 5 is a circuit diagram of an embodiment of an electrosurgical instrument.

A diagram depicting an embodiment of a circuitry design comprising a plurality of electrosurgical paths 130 and an embodiment of a lighting circuit 218 for the instrument 100 is shown in FIG. 5. As previously stated, the handle portion 102 may include a number of electrosurgical paths 130 that are selectively engageable to selectively supply an electrosurgical signal to the electrosurgical electrode 106. Additionally, the handle portion 102 may include a lighting circuit 218, whereby electrical power may be selectively applied to activate a light source resulting in emission of light from the light emitter 300.

FIG. 5 includes electrosurgical equipment comprising an electrosurgical generator 312. The electrosurgical generator 312 may have an electrosurgical cut circuit 210 and an electrosurgical coag circuit 212. The cut circuit 210 and coag circuit 212 may produce different waveforms specific to a cut operation and a coag operation, respectively. The cut circuit 210 may be in electrical communication with a first electrosurgical path 130A (e.g., by way of the connector 128A shown in FIGS. 1A-1D, 3, and 4). The coag circuit 212 may be in electrical communication with a second electrosurgical path 130B (e.g., by way of the connector 128B shown in FIGS. 1A-1D, 3, and 4). The electrosurgical generator 312 may also have an electrosurgery common circuit 214. The common circuit 214 may be in electrical communication with a third electrosurgical path 130C (e.g., by way of the connector 128C shown in FIGS. 1A-1D, 3, and 4). The electrosurgical paths 130A, 130B, and 130C may be defined by a wire, a trace, other conductive element, or any combination of the foregoing.

The first electrosurgical path 130A may be in electric communication with a first contact of a cut switch 232. The third electrosurgical path 130C may be in electrical communication with a second contact of the cut switch 232. Upon closing of the cut switch 232, the cut circuit 210 and common circuit 214 may close and the cut waveform may be activated at the electrode conductor 108. The second electrosurgical path 130B may be in electric communication with a first contact of a coag switch 234. The third electrosurgical path 130C may be in electrical communication with a second contact of the coag switch 234. Upon closing of the coag switch 234, the coag circuit 212 and common circuit 214 may close and the coag waveform may be activated at the electrode conductor 108.

The electrode conductor 108 is represented as a switch in FIG. 5. Thus, when an operational state of the electrosurgical instrument 100 is active and upon contact or near contact of the electrode conductor 108 with the patient 186, current may flow through the electrode conductor 108 to the patient 186 to perform an electrosurgical operation adjacent to the electrode conductor 108. The patient 186 may be connected to the electrosurgical generator 312 by way of a return circuit 216 (e.g., a grounding pad, grounded operating room table, etc.). In turn, electrical current passing through the electrode conductor 108 may flow through the patient to the return circuit 216.

Additionally, FIG. 5 depicts a lighting circuit 218, which may be used to selectively activate the light emitter(s) 300 (e.g., light sources 110 as depicted in FIG. 5). The lighting circuit 218 may also have a light switch 236 which is operative to open and close the lighting circuit 218. Upon closing of the light switch 236, the lighting circuit 218 may be activated to activate the light source (e.g., light sources 110). Thus, the toggle member 112 may be disposed in a position that closes the lighting switch 236 to activate the light sources 110.

The lighting circuit 218 may include one or more batteries 134 arranged in a series or parallel circuit. The positive terminal 182 of the battery may be in electrical communication with a first contact of the light switch 236. The positive leads 166 of each of the light sources 110 may be in electrical communication with a second contact of the light switch 236. The light sources 110 may be provided in a series or parallel lighting circuit 218. The negative leads 168 of the light sources 110 may be in electrical communication with the negative terminal 180 of the batteries 134.

In the illustrated embodiment, the toggle member 112 may have five positions. While these positions are referenced herein as the first through the fifth position, this is for demonstrative purposes only and is not intended to connote any sequence of positions. In this regard, any of the first through fifth positions may be selected in any order without the toggle member 112 passing through any intermediate position to arrive at any given position. That is, any of the positions may be randomly, non-sequentially selected.

In a first position, the toggle member 112 may contact the cut switch 232 to close the cut switch 232. Accordingly, the first position may activate the cut operation of the electrode conductor 108 as the first electrosurgical path 130A and the third electrosurgical path 130C are in turn electrically connected. A second position of the toggle member 112 may contact the coag switch 234 to close the coag switch 234. Accordingly, the second position may activate the coag operation of the electrode conductor 108 as the second electrosurgical path 130B and the third electrosurgical path 130C are in turn electrically connected. A third position of the toggle member 112 may make contact with the cut switch 232 as well as the light switch 236. As such, the cut operation of the electrode conductor 108 may be activated and the light sources 110 may be illuminated. A fourth position of the toggle member 112 may contact the coag switch 234 as well as the light switch 236. Accordingly, the coag operation of the electrode conductor 108 may be activated and the light sources 110 may be illuminated. A fifth position of the toggle member 112 may result in the toggle member 112 only contacting the light switch 236 to close the light switch 236. As such, only the light sources 110 may be illuminated, while no electrosurgical circuit is established.

Wth further reference to FIGS. 3 and 4, the connectors 128A-128C of the plug body 126 may be operatively interconnected to a respective one of the electrosurgical paths 130 which are contained within an insulative cover 132 of the signal cable 124 along substantially all of the length of the signal cable 124. The electrosurgical paths 130 may in turn be in operative communication with a circuit member 150. The circuit member 150 may interact with the toggle member 112 to selectively establish electrical communication between one or more of the electrosurgical paths 130 to activate at least one operational state of the electrosurgical instrument 100. In this regard, various electrosurgical operations (e.g., a cut operation, coag operation, etc.) facilitated by the various electrosurgical paths 130 may be activated using the toggle member 112.

In the particular embodiment illustrated in FIGS. 3 and 4, the toggle member 112 may have a first leg 146 and a second leg 148, each of which is in contact with a toggle receiver 174. The toggle receiver 174 may comprise a portion of a handle chassis 204 and circuit member 150. The handle chassis 204 may be a substantially rigid member which extends along the longitudinal axis 198 of the instrument 100 and comprises a portion of the handle portion 102.

The toggle receiver 174 may include inclined side walls along which the first and second leg 146 and 148 may be positioned. The first leg 146 and second leg 148 may be biased in a spaced apart position. Accordingly, the toggle member 112 may interact with the toggle receiver 174 such that the legs 146 and 148 of the toggle member 112 are urged toward the most spaced apart portion of the toggle receiver 174.

The handle portion 102 comprises an elastomeric material which defines an elastomeric handle portion 136 and includes a correspondingly shaped pocket 206 to receive a portion of the toggle member 112. The pocket 206 of the elastomeric handle portion 136 may help to retain the toggle member 112 in the toggle receiver 174 at the uppermost level thereof as shown in FIG. 2. Additionally or alternatively, a ledge 220 (shown in FIG. 6) may be provided to retain the toggle member 112 in contact with the circuit member 150 at the most spaced apart portion of the toggle receiver 174. The pocket 206 may also maintain the toggle member 112 in a centered position with respect to the toggle receiver 174. This position, shown in FIG. 2 wherein the toggle member 112 is centered with respect to the toggle receiver 174 and residing at the most spaced apart portion of the toggle receiver 174 sidewalls, may be referred to as a home position. When the toggle member 112 is in the home position, the lighting circuit and the electrosurgical circuits may be inactive. As discussed below, the toggle member 112 may be manipulatable away from this home position to activate at least one of the electrosurgical circuits and/or the lighting circuit.

Figure 6:
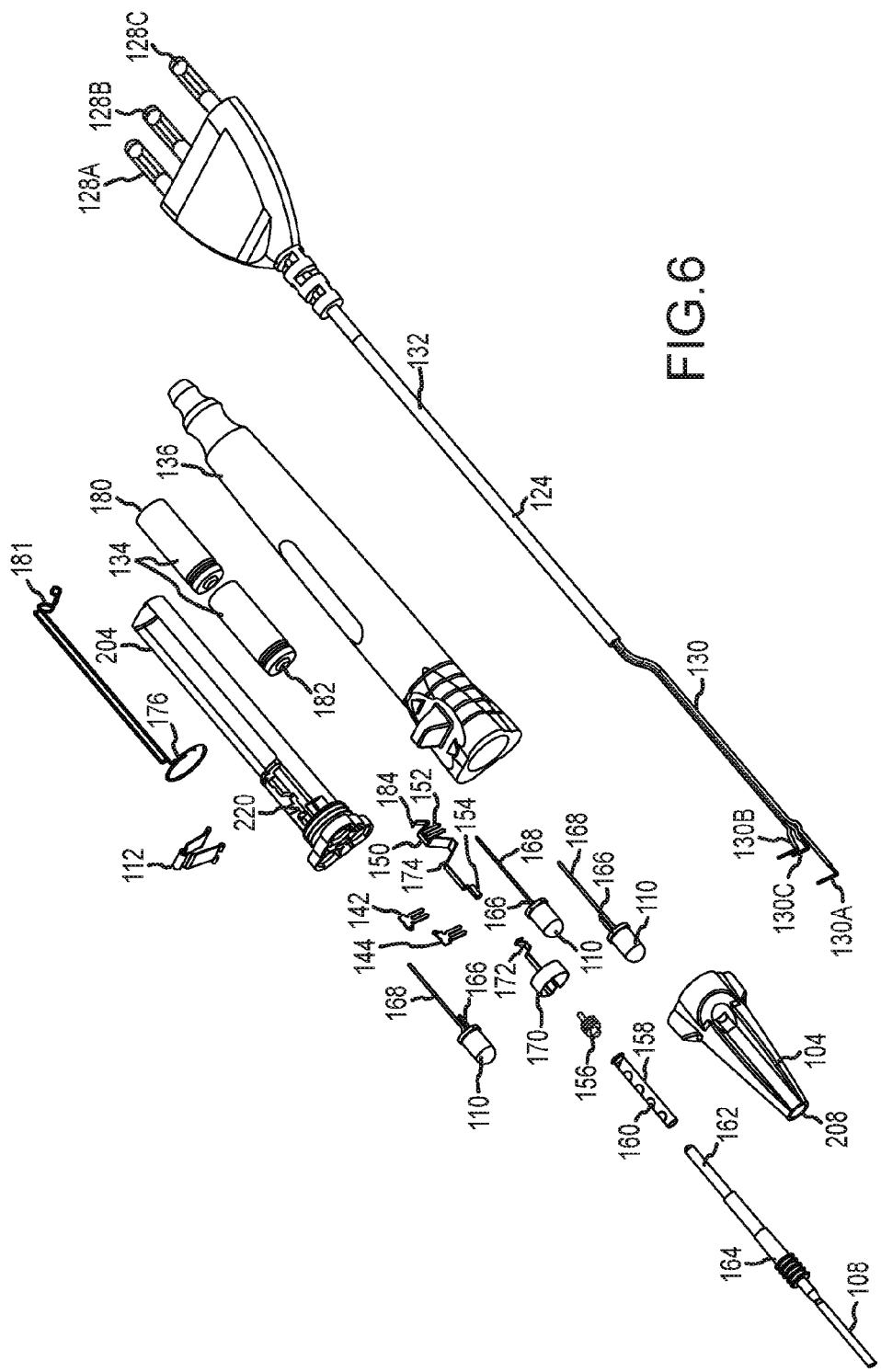
FIG. 6 is an exploded view of an embodiment of an electrosurgical instrument.

Wth reference now to FIG. 6, an exploded view of the embodiment depicted in FIGS. 1A-1D, 3, and 4 is shown. A signal cable 124 may be provided that contains a portion of the electrosurgical paths 130A, 130B, and 130C. The signal cable 124 may also include an insulative covering 132 through which the electrosurgical paths 130A, 130B, and 130C pass. In this regard, connector 128A may be in electrical communication with the first electrosurgical path 130A. Similarly, the connector 128B may be in electrical communication with the second electrosurgical path 130B, and connector 128C may be in electrical communication with the third electrosurgical path 130C.

The first electrosurgical path 130A may be in electrical communication with a cut contact 144. The second electrosurgical path 130B may be in electrical communication with a coag contact 142. The cut contact 144 and coag contact 142 may be disposed on opposite sides of the toggle member 112 and selectively contactable by respective legs 146 and 148 the toggle member 112, as will be discussed in further detail below. The electrosurgical common circuit corresponding to the third electrosurgical path 130C may be in electrical communication with the circuit member 150. The circuit member 150 may comprise a conductive body. The circuit member 150 may include a common contact 152 which is in electrical communication with the third electrosurgical path 130C. The respective electrosurgical paths 130A-130C may, for instance, be pressed into contact with a respective one of the contact members 142, 144, and 152 to establish electrical communication therewith.

Additionally, the circuit member 150 may also have an electrode contact 154 which, when the instrument 100 is assembled, contacts a socket pin 156. The socket pin 156 is in further electrical communication with the conductive electrode socket 158. An aperture 208 of a nose 104 may receivingly engage a proximal end 162 of the electrode conductor 108. As such, the electrode socket 158 provided on the interior of the nose 104 may establish electrical communication between the socket pin 156 and the proximal end 162 of the electrode conductor 108.

An electrode insulator 164 may be disposed about the electrode conductor 108 to provide electrode isolation thereof and may allow for gripping to remove or rotate the electrode conductor 108. The electrode isolator 164 may be slidingly received by the aperture 208 in the nose 104 to further supportably connect the electrode conductor 108. As the electrode conductor 108 may be slidingly received by the electrode socket 158 and nose 104, the electrode conductor 108 may be rotatable in the electrode socket 158 to different angular positions or may be removed and replaced with alternate electrodes. A center axis of the electrode conductor 108 may in turn be aligned with the longitudinal axis 198 of the handle portion 102.

Each light source 110 may include a positive lead 166 and a negative lead 168. The negative lead 168 may extend a greater distance proximately than the positive lead 166 for each of the light sources 110. In this regard, each of the positive leads 166 of the light sources 110 may be in electrical communication with a light source connector ring 170. The light source connector ring 170 may include a toggle contact surface 172 which, when the instrument is assembled, may be aligned with a toggle receiver 174 provided on the circuit member 150. The toggle contact surface 172 may be positioned adjacent to the toggle receiver 174 and be in selective electrical communication with the toggle receiver 174 by way of manipulation of the toggle member 112. The toggle contact surface 172 may correspond to the inclined side walls of the toggle receiver 174. The negative leads 168 of the light sources 110 may be electrically isolated from the light source connector ring 170 and may extend distally to contact a light connector 176. The light connector 176 may include a lead contact ring 178 in electrical communication with the negative lead 168 of the light sources 110. A battery contact 180 may be provided on a proximal end of the light connector 176. The battery contact 180 may be provided in contact with a negative terminal 180 of at least one battery 134 supportably interconnected to the handle chassis 204. As shown, two batteries 134 are provided in series and may be disposed in the handle chassis 204 when the instrument 100 is assembled. Alternatively, the two batteries 134 may be provided in parallel. The positive terminal 182 of the battery 134 or batteries may contact a positive battery contact 184 provided on a proximal end of the circuit member 150.

As shown in FIGS. 4 and 6, the elastomeric handle portion 136 may comprise and extend along substantially all of the handle portion 102. The elastomeric handle portion 136 may form a distal annular seal 140 that may press against a corresponding annular surface of the handle chassis 204 to prevent introduction of fluids into the interior of the elastomeric handle portion 136. Additionally or alternatively, an adhesive or the like may be applied at the interface between the elastomeric handle portion 136 and the annular surface of the handle chassis 204 to provide a permanent distal annular seal 140.

In this regard, any portion of the electrosurgical paths 130 and/or lighting circuit 218 contained in the elastomeric handle portion 136 may remain isolated from fluids (e.g., bodily fluids in contact with the electrosurgical instrument 100 during a procedure, saline introduced to a wound area during a procedure, etc.). This may prevent unintentional activation of one or more of the electrosurgical circuits or lighting circuit due to an electrical short caused by ingress of conductive fluids and may also electrically isolate a user or patient from the circuitry provided in the electrosurgical instrument 100.

Further in this regard, the elastomeric handle portion 136 may extend continually from the proximal end 202 of the handle portion 102 to the distal end 200 of the handle portion 102. The elastomeric handle portion 136 may form a proximal annular seal 138 adjacent to the proximal end 202. The proximal annular seal 138 may be disposed adjacent to where the signal cable 124 meets the handle portion 102. As such, the elastomeric handle portion 136 may press against the insulative covering 132 to form the proximal annular seal 138. Additionally or alternatively, an adhesive or the like may be applied at the interface between the elastomeric handle portion 136 and the insulative covering 132 of the signal cable 124 to provide a permanent proximal annular seal 138.

The elastomeric handle portion 136 may extend in a continuous manner distally from the proximal end 202 of the handle portion 102. The elastomeric handle portion 136 may be correspondingly contoured to the exterior of the handle chassis 204 along the interior surface of the elastomeric handle portion 136. The elastomeric handle portion 136 may provide a gripping surface 206 along the exterior of the elastomeric handle portion 136. The gripping surface 206 may be finished so as to provide a slip resistant surface. This slip resistant surface, along with the elastomeric nature of the elastomeric handle portion 136 may provide a suitable gripping surface for a user to manipulate the instrument 100. The elastomeric handle portion 136 may include a contoured portion 302 accommodating and/or partially defining the surface projections 304.

The elastomeric handle portion 136 may extend continuously over the toggle member 112 so as to define a seal adjacent to the toggle member 112. Therefore, the elastomeric handle portion 136 may facilitate deflection of the toggle member 112 from the home position while maintaining the seal adjacent to the toggle member 112. As such, the toggle member 112 may be allowed to deflect with respect to the handle chassis 204 such that the elastic deflection of the elastomeric handle portion 136 maintains a seal adjacent to the toggle member 112. This, in addition to the foregoing discussion regarding the sealing of the elastomeric handle portion 136 at the proximal end 202 and distal end 200, may effectively include the ingress of fluids into the interior of the elastomeric handle portion 136 so as to maintain electrical isolation of the electrosurgical paths and lighting circuit, and to maintain electrical isolation between the electrosurgical instrument 100 and a user of the electrosurgical instrument 100.

The nose 104 may be supportably connected to and extend distally from the distal end 200 of the handle portion 102. The nose 104 may have a corresponding shape so as to define a conformal transition at the interface between the proximal end of the nose 104 and the distal end of the handle portion 102. That is, the external perimeter shape of the nose 104 may be of the same shape as the external perimeter shape of the distal end 200 of the handle portion 102. The nose 104 may generally taper along its length from the junction of the nose 104 with the distal end 200 of the handle portion 102 in a direction distal to the proximal end of the nose 104. Also, the nose 104 may include tapering ribs 306 extending from the conformal transition between the nose 104 and the handle portion 102. In this regard, each of the ribs 306 may comprise an extended surface corresponding to one of the first side 118, second side 120, or third side 122. As such, corresponding ribs 306 may coordinate with one of the first side 118, second side 120, and third side 122 to provide an extended grip surface extending along the nose 104. Accordingly, a corresponding extended grip surface comprising a rib 306 and one of the sides 118, 120, and 122 may facilitate improved control of the electrosurgical instrument 100 by a user.

In some embodiments, the nose 104 may be light transmissive, e.g., transparent or translucent. As such, the nose 104 may be operative to diffuse or refract light emitted from a corresponding light emission location of the light emitter 300 adjacent to the proximal end of the nose 104. The nose 104 may be supportably connected to the handle chassis 204. This connection of the nose 104 to the handle chassis 204 may use any appropriate joining mechanism, including press fits, adhesives, ultrasonic welding, etc. In any regard, the interface of the nose 104 and the handle portion 102 may also be sealed to prevent ingress of fluids into the interior of the handle portion 102. Additionally, the nose 104 may include one or more light openings 308 may be provided in the nose 104. Corresponding light openings 308 may be provided for each light emission location of the light emitter 300. For instance, in the embodiment depicted wherein light sources 110 define the light emitter 300, at least a portion of each of the light sources 110 may extend into a corresponding light opening 308. The interface between the light opening 308 and the light source 110 extending there through may be sealed (e.g., by way of an interference fit, adhesives, etc.).

Figure 7A:
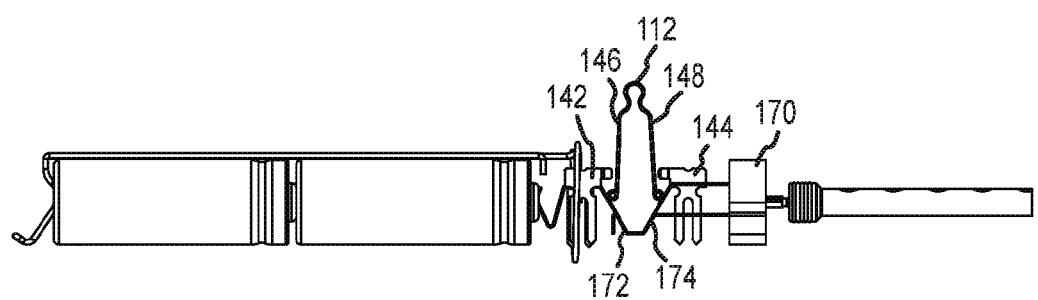
FIGS. 7A-7F are cut away views of a toggle member of an embodiment of an electrosurgical instrument in various positions.

FIGS. 7A-7F demonstrate the various positions of the toggle member in one embodiment. In FIG. 7A, the toggle member 112 may be in a home position. The first leg 146 and second leg 148 of the toggle member 112 may be resting against the toggle receiver 174 above a level where the toggle contact surface 172 is adjacently disposed. In turn, the lighting circuit may remain open and the light sources 110 may remain inactive. As previously discussed, the inclined side walls of the toggle receiver 174 may bias the toggle member 112 away from the toggle contact surface 172 at the most spaced apart portion of the inclined walls of the toggle receiver 174. For instance, in one embodiment, the toggle member 112 may be prevented from moving further away from the toggle contact surface 172 by way of the elastomeric handle portion 136. Additionally or alternatively, a ledge 220 (shown in FIG. 6) on the handle chassis 204 may be provided to limit the extent of travel of the toggle member 112 at the uppermost level of the toggle receiver 174. An elastomeric handle portion 102 may also maintain the toggle member 112 in the home position as shown in FIG. 7A by centering the toggle member 112 in the home position such that neither the first leg 146 nor second leg 148 contacts either the cut or coag contacts 144 or 142. In this regard, the angle of the toggle member 112 with respect to the handle chassis 204 in a proximal and distal respect may be maintained.

Figure 7B:
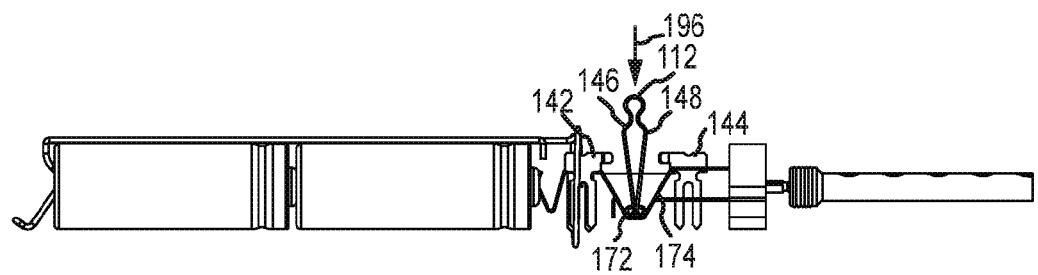

As shown in FIG. 7B, a depressive force 196 may be applied radially to the toggle member 112 with respect to the longitudinal axis 198. Accordingly, the toggle member 112 may be displaced with respect to the toggle receiver 174. In this regard, the first leg 146 and second leg 148 of the toggle member 112 may be urged towards each other. The first leg 146 and second leg 148 may be displaced to a level below where the toggle contact surface 172 is adjacent to the toggle receiver 174 such that the legs make contact with the toggle contact surface 172 disposed adjacent to the bottom of the toggle receiver 174. Correspondingly, the lighting circuit 218 may be completed as the toggle member 112 allows current to flow between the circuit member 150 and the light source connector ring 170 shown in FIG. 6. Accordingly, the position of the toggle member 112 shown in FIG. 7B represents the toggle member 112 in a position wherein only the lighting circuit is established. As can be seen, the coag contact 142 and cut contact 144 may not be contact the toggle member 112 when in this position. Furthermore, as the first leg 146 and second leg 148 of the toggle member 112 are urged together by the relative displacement of the toggle member 112 with respect to the inclined side walls of the toggle receiver 174, the distance between the toggle legs 146 and 148 and a respective contact is increased. This may help to reduce the likelihood that the electrode conductor 108 is activated in either the cut or coag operation when a user desires only the lighting circuit 218 to be active. As such, the electrode conductor 108 may not receive an electrosurgical signal and the lighting circuit 218 may be the only active circuit in the instrument when the toggle member 212 is disposed as shown in FIG. 6B.

Figure 7C:
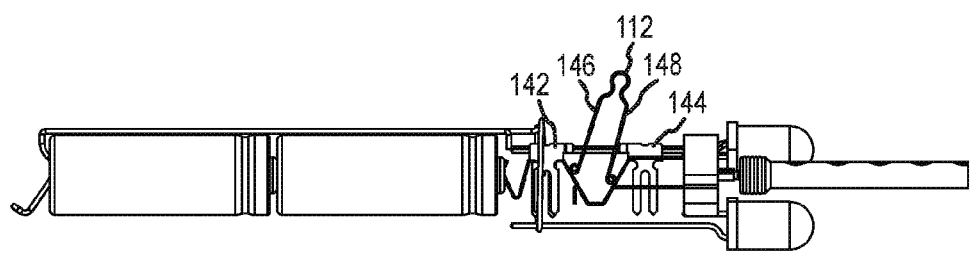

In FIG. 7C, the toggle member 112 is displaced distally such that the second leg 148 of the toggle member contacts the cut contact 144. As such, electrical communication may be established between the cut contact 144 and the second leg 148 of the toggle member 112. Because the toggle member 112 also contacts the circuit member 150, electrical communication may also be established between the first leg 146 of the toggle member 112 and the third electrosurgical path 130C. As such, the first leg 146 of the toggle member 112 establishes electrical communication between the first electrosurgical circuit 130A and the third electrosurgical circuit 130C such that the cut circuit 210 is in electrical communication with the electrode conductor 108. In this regard, once the electrode conductor 108 makes near contact with the patient, the waveform generated by the cut circuit 210 may be applied the patient to perform a cut operation.

Figure 7D:
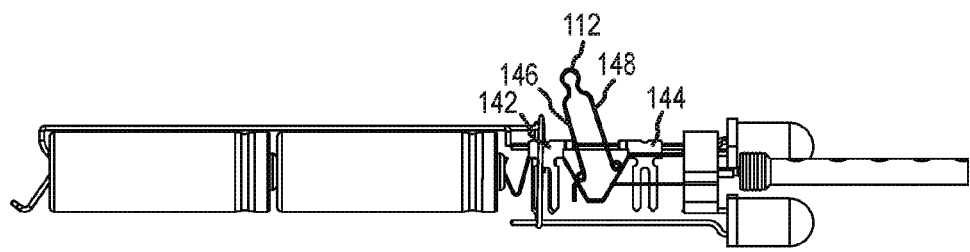

FIG. 7D illustrates a position of the toggle member 112 wherein the coag circuit 212 is in electrical communication with the electrode conductor 108. As shown, the toggle member 112 may be displaced distally such that the first leg 146 of the toggle member 112 comes into contact with the coag contact 142. As the second leg 148 of the toggle member 112 maintains contact with the toggle receiver 174, which is in electrical communication with the third electrostatic path 130C, the coag circuit 212 may be in electrical communication with the electrode conductor 108 such that if the electrode conductor 108 comes in near contact with the patient 186, the waveform generated by the coag circuit 212 may pass through the patient 186 to perform a coag operation.

Figure 7E:
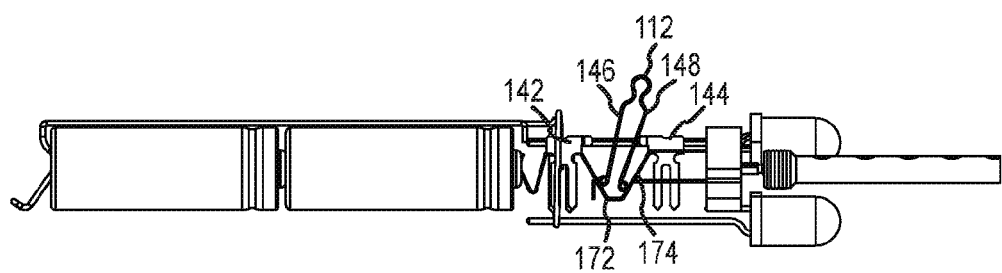

FIG. 7E depicts a position of the toggle member 112 wherein both the lighting circuit 218 is activated in addition to the cut circuit 210 being in electrical communication with the electrode conductor 108. In this regard, the toggle member 112 may be displaced such that the toggle member 112 contacts the toggle contact surface 172 to activate the lighting circuit 218 as described above with respect to FIG. 7A. In addition, the toggle member 112 and may be displaced proximally such that the second leg 148 of the toggle member 112 may also contact the cut contact 144 thus enabling a cut operation by applying the waveform generated by the cut circuit 210 to the electrode conductor 108.

Figure 7F:
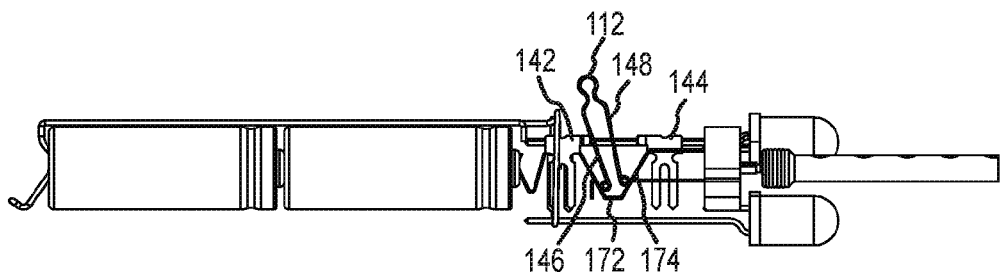

FIG. 7F depicts a position of the toggle member 112 wherein the toggle member 112 is manipulated to both activate the lighting circuit 218 as well as establish electrical communication between the coag circuit 212 and the electrode conductor 108. In this regard, the toggle member 112 may be displaced by the depressive force 196 such that the toggle member 112 contacts the toggle contact surface 172 to activate the lighting circuit 218. In addition, the toggle member 112 and may be displaced proximally such that the first leg 146 of the toggle member 112 is in contact with the coagulation contact 142. The second leg 148 of the toggle member 112 may maintain contact with the toggle receiver 174 which is in turn in electrical communication with the third electrosurgical path 130C. As such, the coag circuit 212 is in electrical communication with the electrode conductor 108 such that a waveform generated by the coag circuit 212 may pass through the patient 186 upon near contact with the electrode conductor 108.

In this regard, when in the positions shown in FIGS. 7E and 7F, the toggle member 112 may be displaceable in two dimensions. A first dimension may correspond to the proximal and distal movement of the toggle member 112 to establish contact between the coag contact 142 and the cut contact 144, respectively. In this regard, the first dimension may be parallel to the longitudinal axis 198 of the instrument 100. The toggle member 112 may be displaced in a second dimension to activate the lighting circuit 218. This second dimension may be substantially perpendicular to the longitudinal axis 198 of the instrument 100 such that the toggle member 112 is depressed within the toggle receiver 174 to activate the lighting circuit 218. As such, the second dimension may correspond to depression of the toggle member 112 with respect to the handle chassis 204.

Figure 8:
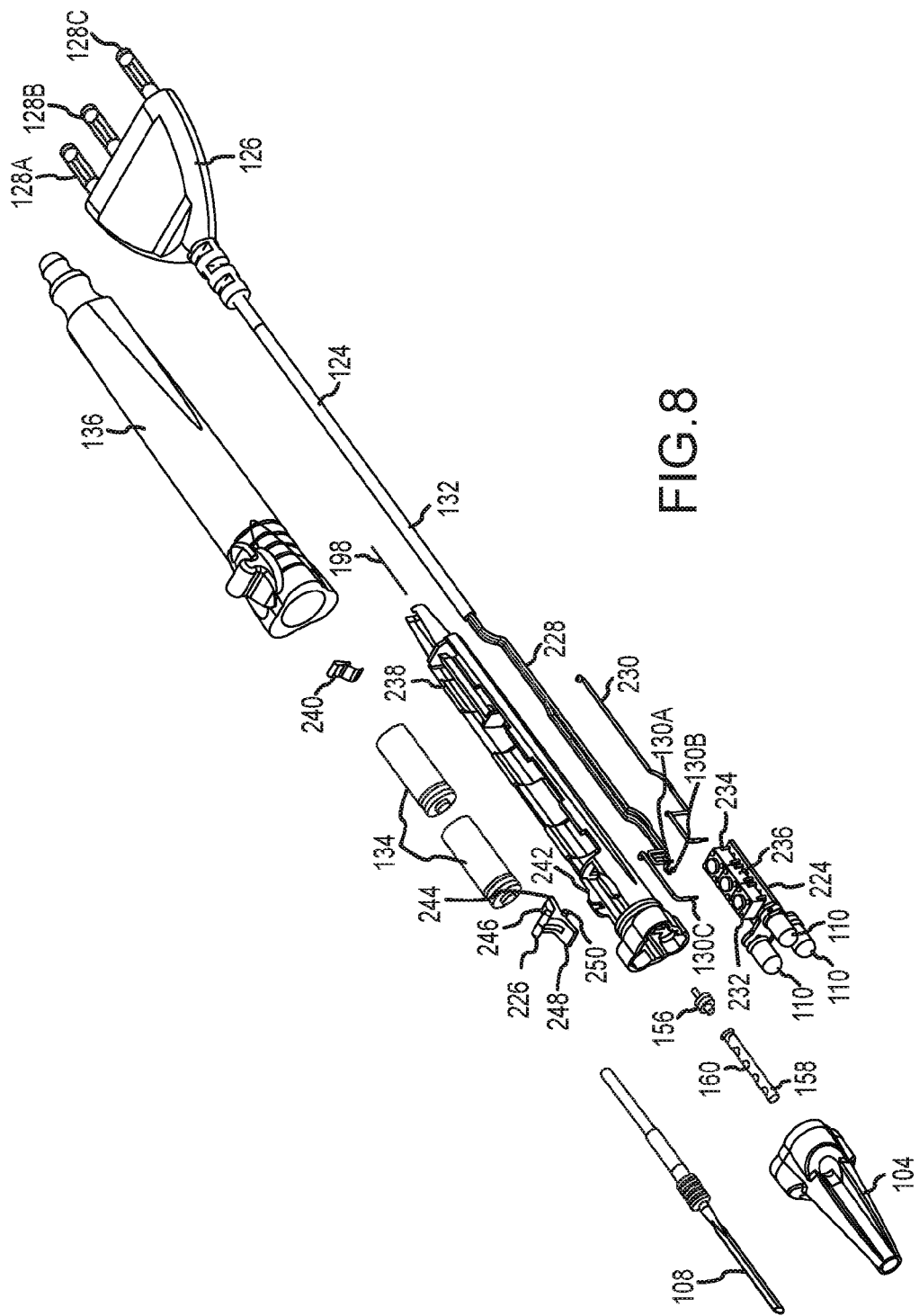
FIG. 8 is an exploded view of another embodiment of an electrosurgical instrument.

Turning to FIG. 8, another embodiment of an electrosurgical instrument 222 is depicted. The instrument 222 may include a toggle member 226 which includes a toggle beam 244 which extends proximally in a direction generally parallel with the longitudinal axis 198 of the instrument 222. The toggle beam 244 may have a proximal beam portion 246 and a distal beam portion 248. The toggle member 226 may also include a center protrusion 250 which extends downward from the toggle member 226 in a direction perpendicular to the toggle beam 244. The toggle member 226 may be supportably connected to a handle chassis 238 at a vertical slot 242. The slot 242 may accommodate a floating pivot that allows the toggle beam 244 to be displaced toward and away from a printed circuit board (PCB) 224. This floating pivot also allows the toggle beam 244 to pivot about the floating pivot point in a "see-saw" like manner. As such, the proximal beam portion 246 and distal beam portion 248 may be selectively advanced toward the PCB 224 upon the beam member 226 pivoting about this floating fulcrum.

The PCB 224 may include a plurality of contact switches similar to those described above with regard to FIG. 5. For instance, momentary contact switch modules or snap dome switches may be provided. These switches may be normally open switches which close upon contact with the toggle member 226. In one embodiment, the activation force is usually not less than about 100 g and not more than about 500 g, however, other activation forces may be used to provide different tactile feedback upon activation of the switches. These switch modules may allow for selective activation of one or more of a coag operation, a cut operation, and a lighting circuit as discussed above with respect to FIG. 5. For instance, a cut switch 232, a light switch 236, and a coag switch 234 may be arranged on the PCB 224 such that the light switch 236 is disposed between the cut switch 232 and the coag switch 234, which are respectively positioned distally and proximally from the light switch 236. The cut switch 232, lighting switch 236, and coag switch 234 may be aligned with the distal beam portion 248, center protrusion 250, and proximal beam portion 246, respectively.

In this regard, upon depression of the toggle member 226 within the vertical slot 242, the center protrusion 250 may contact the light switch 236. In turn, the light switch 236 may close. In this regard, a lighting circuit may be completed, resulting in the activation of one or more light sources. The light sources 110 may be in electrical communication with the PCB 224. A positive terminal 182 of one or more batteries 134 arranged in series or parallel may also be in electrical communication with the PCB 224. A battery lighting path 230 (e.g., comprising a wire, trace, or other conductive body) may establish electrical communication between the PCB 224 and a battery contact 240 in electrical communication with a negative terminal 180 of the one or more batteries 134. As such, upon contact of the central protrusion 250 with the light switch 236, a lighting circuit may be closed so that the light sources 110 are activated.

Additionally, a first electrosurgical path 130A, a second electrosurgical path 130B, and a third electrosurgical path 130C may be provided. These paths 130A-130C may be in respective communication with connectors 128A-128C and in turn electrosurgical signals generated by electrosurgical equipment (not shown), in a similar regard as described above. The first electrosurgical path 130A may correspond to the cut switch 232 such that when the cut switch 232 is closed, the cut signal 210 is supplied to a socket pin 156, conductive material 160, and electrode conductor 108 as described above. Accordingly, when the toggle member 226 is displaced distally with respect to the handle chassis 238, the toggle beam 244 may pivot about the floating pivot such that the distal beam portion 248 comes into contact with the cut switch 232. In this regard, distal displacement of the toggle member 226 may result in activation of a cut operation.

Similarly, the coag switch 234 may be in communication with the second electrosurgical path 130B. Upon closing of the coag switch 234, the coag signal 212 may be activated at the electrode conductor 108. In turn, the toggle member 226 may be displaced proximally such that the toggle beam 244 pivots about the floating pivot in the vertical slot 242 and the proximal beam portion 246 is advanced toward the coag switch 234. The proximal beam portion 246 may contact the coag switch 236 to activate a coag operation.

In this regard, motion of the toggle member 226 in the second dimension perpendicular to the longitudinal axis 198 of the instrument 222 results in the center protrusion 250 contacting the lighting switch 236 to activate the light sources 110. This may be performed in isolation or in conjunction with either proximal or distal advancement of the toggle member 226 in the first dimension parallel to the longitudinal axis 198 by virtue of the floating pivot. As such, the cut switch 232 and light switch 236 may be activated simultaneously by the distal beam portion 248 and center protrusion 250, respectively. Additionally, the coag switch 234 and the light switch 236 may be activated simultaneously by the proximal beam portion 246 and central protrusion 250, respectively. In this regard, the functionality associated with the five toggle member positions described above may also be realized with toggle member 226.

FIGS. 9A, 9B, 9C, and 9D illustrate various views of another embodiment of a hand-held instrument 401 intended for medical-related use. By way of primary example, hand-held instrument 401 may be utilized for smoke evacuation of a patient tissue site at which a medical procedure is conducted via the application of energy to the tissue site. As may be appreciated, energy application may generate smoke which may obscure the tissue site and/or otherwise result in undesirable environmental conditions for medical personnel and the patient. Additional applications and modifications of the hand-held instrument 401 will become apparent upon further description.

Hand-held instrument 401 may include a housing 410 sized for hand-held use and defining a portion or all of an internal volume. In the illustrated embodiment, housing 410 is of an elongate and cylindrical configuration to facilitate single hand manipulation by a user. The hand-held instrument 401 includes a proximal end 403 and a distal end 405. A gas inlet port 420 is provided proximate to the distal end 403, and a gas outlet port 430 is provided along an outer side wall of housing 410, proximal to the inlet port 420. As will be further described, in operation, smoke-laden gas may be drawn in to inlet port 420, pass through an internal volume of hand-held instrument 401, and exhausted through outlet port 430 to improve visual observation of a tissue site. Further, outlet port 430 may be provided with smoke filtration functionality to reduce undesirable airborne smoke constituents, thereby improving environmental conditions at a medical procedure site.

In the illustrated embodiment, housing 410 may comprise a first member 412 that includes the outlet port 430, and a second member 414 that includes the inlet port 420. The first member 412 may be sized and contoured for single hand manipulation of the hand-held instrument 401 by a user, wherein inlet port 420 may be positioned where desired relative to a smoke source (e.g., at a surgical tissue site). As shown, first member 412 and second member 414 may have cylindrical outer configurations.

The first member 412 and the second member 414 may be interconnected and disposed for relative movement therebetween, thereby facilitating user selected positioning of the inlet port 420 relative to the first member 412. For example, the first member 412 and second member 414 may be provided for relative movement therebetween along a longitudinal axis of the hand-held instrument 401. FIGS. 9A and 9B illustrate the second member 414 selectively positioned in an extended first position relative to first member 412. As shown in FIG. 9C, the second member 414 is selectively positioned in a retracted second position relative to first member 412. Such relative positioning may be provided by slidably positioning a proximal end portion of second member 414 within a distal end portion of the first member 412, wherein the second member 414 may be selectively and advantageously positioned at any one of a continuum of positions selected by a user.

As will be further described, hand-held instrument 401 may include internal componentry for inducing gas flow in to inlet port 420, through an internal volume of hand-held instrument 401, and out of outlet port 430. In particular, and as shown in FIG. 9D, an impeller 460 may be disposed within housing 410 between inlet port 420 and outlet port 430 and rotatively powered by an on-board motor (not shown) to draw gas in to inlet port 420. One or more hand control switches 450 may be provided on housing 410 for user control of the motor, e.g., to start and stop motor operation. Such hand control switches 450 may be conveniently located on a side wall portion of first member 412.

The hand-held instrument 401 may be optionally provided to include an integrated energy emission component. Such energy emission component may be provided for use in energy application to a patient tissue site in connection with a medical procedure. By way of example, the energy emission component may comprise one of the following: an electrosurgical electrode, a laser beam emitter (e.g., for ultrasonic tissue cutting and/or tissue sealing).

In the illustrated embodiment, hand-held instrument 401 optionally includes an electrosurgical electrode 440 supportably interconnected to housing 410 at the distal end 403 thereof. For example, the electrosurgical electrode may be interconnected to second member 14 for co-movement therewith. As illustrated, the electrosurgical electrode 440 may be provided to extend distally beyond the inlet port 420, wherein during use the electrosurgical electrode 440 may apply an electrosurgical signal to a tissue site and hand-held instrument 401 may conveniently provide for evacuation of smoke generated in conjunction therewith. In that regard, electrosurgical electrode 440 may be disposed parallel to a longitudinal axis of and gas-flow path through the hand-held instrument 401, thereby facilitating contemporaneous desired positioning of hand-held instrument 401 for both energy application and smoke evacuation.

Figure 11:
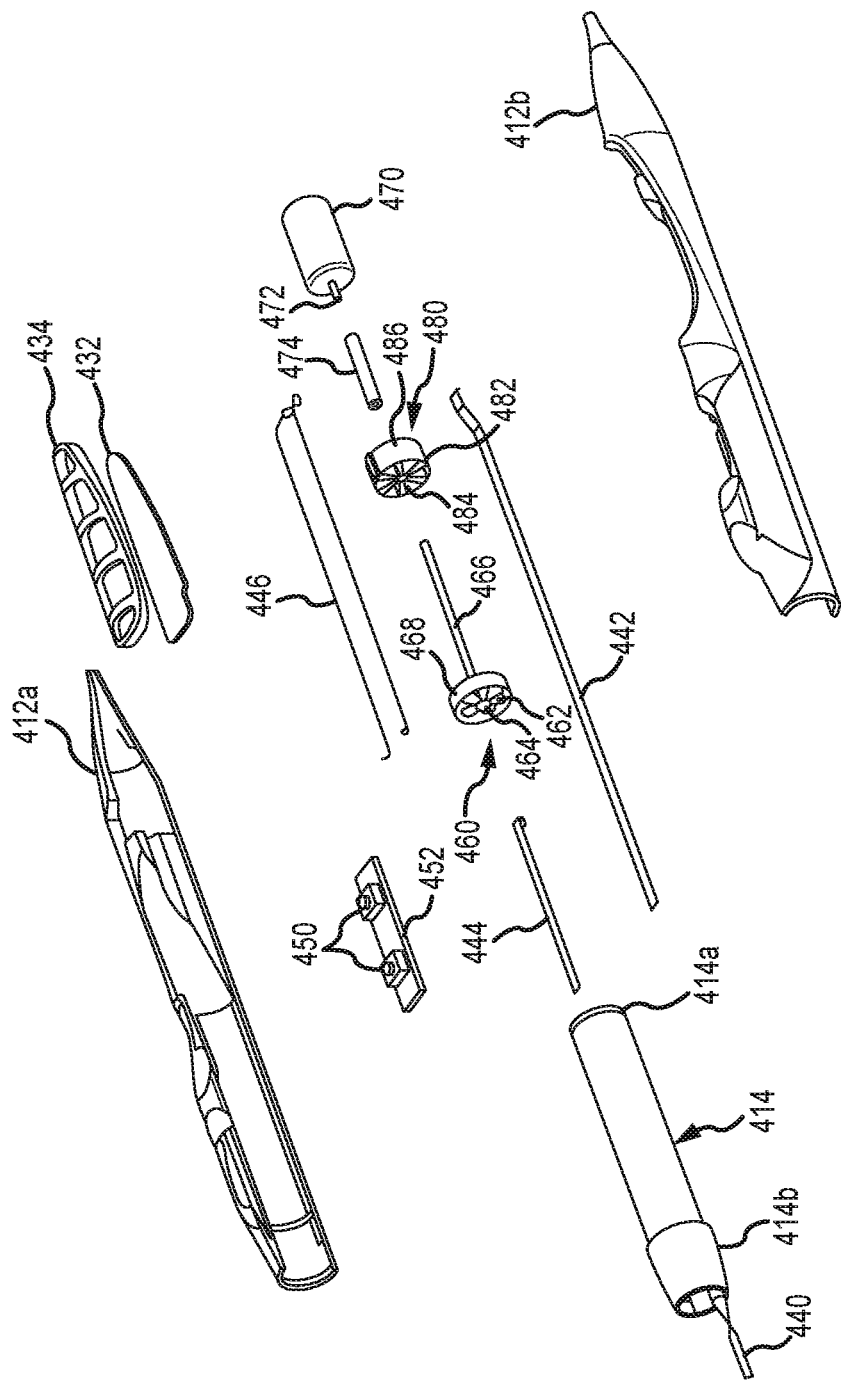
FIG. 11 is an exploded view of components of the hand-held instrument embodiment of FIG. 9A.

Reference is now made to FIGS. 10A, 10B, and 11 which illustrate internal components of hand-held instrument 401. Such components may include the impeller 460 and a motor 470 operatively interconnected with the impeller 460 to rotate the impeller 460. The impeller 460 may include a plurality of blades 462 extending outward from and spaced about a hub 464, wherein the blades may comprise angled surface portions that extend laterally across an internal volume of the hand-held instrument so as to draw gas into inlet port 420 upon rotation. Hub 464 may be interconnected to a shaft 466 that may extend proximally and interconnect with output shaft 472 of motor 470 via a coupler 474. The impeller 460 may be supportably disposed within an outer ring member 68 that is fixedly positioned relative to an internal surface of first member 412.

In the illustrated embodiment, housing 410 defines an internal volume comprising a first portion 418a located on a proximal side of impeller 460 and a second portion 418b located on a distal side of impeller 460. As shown, the second portion 418b of the internal volume may be cylindrical and may be combinatively defined by the first member 412 and the second member 414. The first portion 418a may be defined by first member 412 and configured to facilitate gas flow from impeller 460 to outlet port 430.

In that regard, and as shown in FIG. 10A, the first member 412 may be provided with an internal surface that angles (e.g., along a smooth curve) from a first side portion 416a to a proximally and radially offset second side portion 416b to define an angled, proximal end wall of internal volume 482, wherein gas flow from impeller 460 to outlet port 430 is enhanced. In the illustrated embodiment, second side portion 416b is proximally offset and radially offset (e.g., 180° relative to a longitudinal axis of hand-held instrument 401) from first side portion 416a. As shown in FIG. 10B, first member 412 may be also provided with internal surfaces that angle (e.g., along smooth curves) from both a third side portion 416c and radially offset fourth side portion 416d proximally toward a longitudinal axis of hand-held instrument 401 to further enhance gas flow from impeller 460 to outlet port 430. As shown, third side portion 416c and fourth side portion 416d may be radially offset (e.g., 180° relative to a longitudinal axis of hand-held instrument 401), and third side portion 416c and fourth side portion 416d may each be radially offset 90° relative to first side portion 416a and second side portion 416b. As described, the first member 412 may be provided with internal surfaces that collectively define a portion of an elliptic parabaloid.

Hand-held instrument 401 may further include a flow path member 480 for directing gas flow, i.e., to enhance laminar gas flow, proximal to impeller 460. The flow path member 480 may comprise a plurality of spaced vanes 482 having surfaces that extend proximally along and in corresponding directions parallel to a longitudinal axis of the hand-held instrument 401 from a distal end of of the flow member 480 to a proximal end thereof. The surfaces of vanes 482 function to direct gas flow along the longitudinal axis of the hand-held instrument 401. As shown, the vanes 482 may extend outward from and may be spaced about a hub 484 through which output shaft 472 may rotatably extend. The flow path member 480 may include an outer ring 486 that is fixedly positioned relative to an internal surface of first member 412. In that regard, in addition to enhancing laminar gas flow, the flow path member 482 may also act as a bearing surface to provide support and stability for motor output shaft 472.

As noted above, outlet port 430 may be provided with gas filtering functionality. In that regard, a gas permeable, filter element 432 may be provided with a filter frame 434 across an opening on a side wall portion of first member 412. The filter element 432 may be pleated to increase the filter surface area. By way of example, the filter element 432 may be a hepa filter of fiberglass and/or paper construction. In some embodiments, the filter element 432 may be provided to filter particles having a minimum cross-dimension of 0.412 micron or larger. The filter frame 434 may be provided for snap-fit engagement with a side wall portion of first member 412 surrounding the opening therethrough. The filter frame 434 may be removable/replaceable to permit replacement of filter element 432.

In various implementations, the motor 470 may comprise a brushless DC motor or brushed DC motor. As illustrated in FIGS. 10A and 10B, the motor 470 may be located within first member 412 at a distal end thereof. For example, and as best shown in FIG. 10B, the first member 412 may be internally configured to define an internal pocket and channel sized to retainably receive motor 470 and output shaft 472, respectively. Further, the first member 412 may be internally configured to provide the first portion 482 having the surface configuration described above. To provide such internal configurations, first member 412 may be of a molded, two-part construction, wherein a molded first side member 412a and molded second side member 412b may be configured as shown in FIG. 11 and adjoined after positioning of the various described internal components therein. The second member 414 may be of a molded, tubular construction, wherein a proximal end of the second member 414 may be positioned between the two members 412a, 412b of the first member 412 prior to their interconnection. As illustrated, the first member 412 may be provided with an inward-projecting flange 412c at a distal end and the second member 414 may be provided with an outward projecting flange 414a at a proximal end to restrict removal of the second member 414 from within the distal end of the first member 412. Such flanges 412c and 414a may also be sized to permit sliding movement of second member 414 relative to first member 412, while providing for sufficient engagement so as to maintain a selected relative position of first member 412 and second member 414. Further, the second member 414 may be provided with an enlarged, outward projecting distal end 414b to restrict distal travel of the second member 414 relative to the first member 412.

As noted above, one or more switches 450 (e.g., push or toggle switches) may be provided to control operation of motor 470. In that regard, one or more switches 450 may be located within a protective encasement (e.g., having an elastomeric outer layer). The switches may be electrically interconnected to a circuit board 452 that is electrically connected via electrical connection lines to motor 470.

As further noted above, hand-held instrument 1 may optionally include an energy emission component, and in embodiments shown herein, an optional electrosurgical electrode 440 is included. In that regard, reference is now also made to FIG. 12 which illustrates hand-held instrument 401, wherein electrosurgical electrode 440 is electrically interconnected to electrical cabling 490 that extends proximally from the proximal end 403 of hand-held instrument 401 for interconnection to a standard electrosurgical generator via coupler end 492. The electrical cabling 490 and coupler end 492 may be provided for selection and transmission of electrosurgical tissue cutting and tissue coagulation signals from a standard electrosurgical generator. For signal selection, the electrical cabling 490 may be electrically interconnected within hand-held instrument 401 via one or more conductor member 446 and circuit board 452 to switches 450, wherein one of the switches 450 may be utilized to selectively initiate/terminate the provision of an electrosurgical tissue cutting signal to electrode 440, and wherein another one of the switches 450 may be utilized to selectively initiate/terminate the provision of an electrosurgical tissue coagulation signal to electrode 440. Electrical interconnections within the hand-held instrument 401 may be provided so that, upon the provision of an electrosurgical tissue cutting signal or the provision of an electrosurgical tissue coagulation signal, operation of motor 470 is also initiated. Correspondingly, the electrical componentry may be provided so that upon termination of the provision of an electrosurgical tissue cutting signal or termination of an electrosurgical tissue coagulation signal, operation of the motor 470 may terminate. To provide power to the motor 470, separate electrical cabling 500 may proximally extend from the proximal end 443 of hand-held instrument 401 for separate interconnection to an appropriate energy source via plug-in coupler 502. Alternatively, hand-held instrument 401 may include one or more batteries to power motor 470, or in another arrangement electrical cabling 500 may be routed with electrical cabling 490, wherein coupler end 492 may include one or more batteries (e.g., replaceable batteries) for powering motor 470.

In contemplated implementations, the hand-held instrument 401 may provide for gas flow in to inlet port 420 and out of outlet port 430 at a rate of at least 3.0 ft.$^3$/min. For such purposes, second portion 418b of the internal volume may have a diameter of at least 0.5 in. along the length thereof and motor 470 may be provided to rotate impeller 460 at a rate of at least 15,000 revolutions per minute, so as to yield an internal gas flow speed of at least 150 ft./min.

As noted above, electrosurgical electrode 440 may be electrically interconnected to electrical cabling 490. In that regard, and with reference to FIGS. 10A, 10B, and 11, such electrical interconnection may be provided by a first electrical contact 442 and a second electrical contact 444. The first electrical contact 442 may be in the form of an elongate metal strip mounted to an internal surface of the first member 412 so as to extend from a proximal end portion thereof to a distal end portion thereof (e.g., parallel to a longitudinal axis of interfacing portions of first member 412 and second member 414). The second electrical contact 444 may be in the form of a metal strip mounted to an internal surface of second member 414 and extend from a proximal end portion thereof to a contact engagement interface with electrode 440. The second electrical contact 444 may be provided so as to slidably engage the first electrical contact member 442, wherein upon selective positioning of second member 414 relative to first member 412 by a user, the second electrical contact member moves in tandem with the second member 414 while maintaining contact engagement with the first electrical contact 442.

Figure 12:
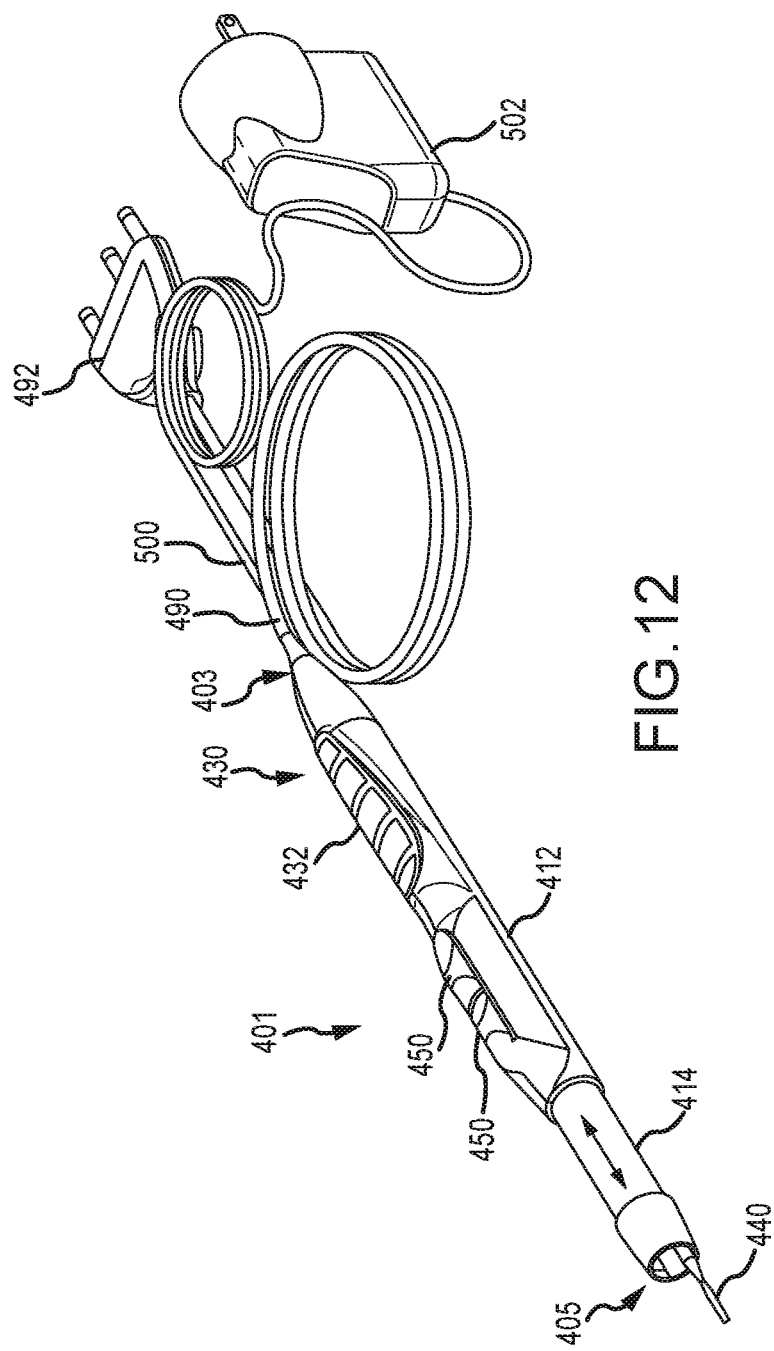
FIG. 12 is a perspective view of the hand-held instrument embodiment of FIGS. 9A-9D, integrated with electrosurgical componentry in an electrosurgical application.

Reference is now made to FIG. 13 which illustrates certain modifications to the hand-held instrument 401 illustrated in FIG. 12. In the modified embodiment, first member 412 of housing 410 may include a bottom channel portion 417 at a distal end for slidably receiving a proximal end portion of a mount 418 that is provided on second member 414 of housing 410. The mount 418 may be provided to support electrosurgical electrode 440 below the inlet port 420 to facilitate laminar gas passage through the internal volume of housing 410.

As described above, the second member 414 may be selectively advanced and retracted relative to the first member 412 along the longitudinal axis of the hand-held instrument 401. Such relative positioning allows the second member 414 and electrosurgical electrode 440 supported thereby to be selectively and advantageously positioned at any one of a continuum positions selected by a user. In the arrangement of FIG. 13, the electrode 440 may extend through mount 418 and engage second electrical contact 444 (not shown) that extends along and is supported by the second member 414, as described above. In turn, a proximal end of second electrical contact 444 may slidably engage the first electrical contact 442 (not shown) that extends along and is supported by the first member 412 as described above.

In another modification to the hand-held instrument shown in FIG. 12, the hand-held instrument of FIG. 13 provides for routing of electrical cabling 490 (not shown) and electrical cabling 500 (not shown) within a common insulative sheath 510 that extends from a proximal end of the hand-held instrument 401 to a distal end that includes coupler end 492 and an adjoined battery module 520. The coupler end 492 may be provided to interface with (e.g. plug in to) a standard electrosurgical generator for the transmission of electrosurgical tissue cutting and tissue coagulation signals via electrical cabling 490, as described hereinabove.

The battery module 520 may be provided for supporting one or more batteries (e.g. two batteries shown in FIG. 13) for providing electrical power (e.g. a 6.0 volt DC signal) to power operation of the motor 470 via electrical cabling 500. The battery module 520 may be provided to facilitate ready placement and replacement of the batteries. For example, as shown in FIG. 13 the battery module 520 may include tubular supports 522 and for slidable placement of batteries thereinto and slidable removal of batteries therefrom. The provision of battery module 522 at a location spaced from the housing 410 of electrosurgical instrument facilitates compliance with sterilization requirements.

Reference is now made to FIG. 14 which illustrates the modified hand-held instrument 401 shown in FIG. 13 with the further inclusion of a plurality of light emitters 550 supportably interconnected to and outside of the second member 414 near a distal end thereof. The light emitters 550 emit light in a direction distal to the distal end of second member 540. The light emitters 550 may be supported by support hubs 419 provided on the second member 414. In one approach, the light emitters 550 may each comprise a light emitting diode (LED).

While two emitters 550 are shown in FIG. 14, it is contemplated that three emitters may be provided in spaced relation about the second member 414 (e.g. offset about 120° relative to each other in a ring-like configuration). The provision of light emitters 550 at the distal end of the hand-held instrument 401 may provide for the illumination of a volume that includes at least a portion of the electrode 440 (e.g. at least a distal end portion of electrode 440), thereby facilitating electrosurgical procedures. Further, the provision of a plurality of light emitters 550 located about the second member 414 may provide for optimal illumination of a volume by avoiding or substantially reducing any "shadowing" effects resulting from the projecting electrosurgical electrode 440 and/or the distal end of the second member 414.

The light emitters 550 may be powered and selectively turned on and off in tandem with and in the same manner as described above in relation to the powering and operation of the motor 470. In that regard, the light emitters 550 may be electrically interconnected for receiving a power signal in tandem with motor 470, as controlled by one of the switches 450. In other arrangements, switches 450 may be provided to facilitate separate on/off control of the motor 470 and light emitters 550.

Figure 15:
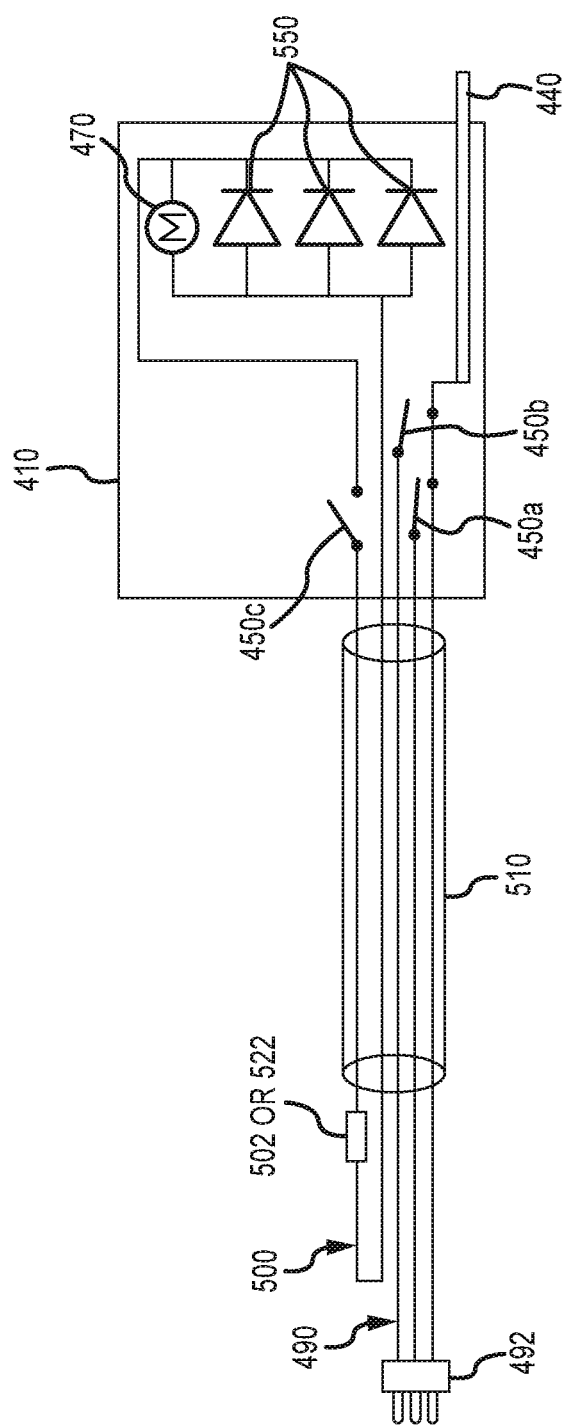
FIG. 15 is a schematic illustration of hand-held instrument showing electrical connections of powered components.

Reference is now made to the schematic illustration of FIG. 15 which illustrates electrical connections for components of the hand-held instrument 401 described hereinabove. In particular, in relation to each of the described arrangements, housing 410 houses motor 470 that may be powered via electrical cabling 500 by either use of plug-in coupler 502 (e.g. an AC/DC converter transformer) at an external energy source (e.g. a 110 Volt AC source), or by one or more batteries (e.g. to provide a 6 volt DC signal) located at battery module 522. To provide for on/off control of motor 470, switches 450 may include switch 450c at housing 410 for selective operator control.

Further, an electrosurgical electrode 440 may be supportably interconnected to housing 410 and powered via electrical cabling 490 by use of a coupler end 492 at an electrosurgical generator. The electrosurgical generator may provide tissue cutting and tissue coagulation signals via separate electrical lines comprising electric cabling 490. Selective operator control over the provision of either a tissue coagulation signal to electrode 440 or a tissue cutting signal to electrode 440 may be provided via the provision of switches 450a and 450b at housing 410. For the hand-held instrument 401 shown in FIG. 14, light emitters 550 may be housed in housing 410 and powered in tandem with motor 470 via electrical cabling 500 by either plug-in coupler 502 or by one or more batteries located at battery module 522, as described above in relation to the powering of motor 470. To provide for on/off control of the light emitters 550, switch 450c may be utilized. In other arrangements, switches 450 may include a separate additional switch for selective on/off control of light emitters 550.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain known modes of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

What is claimed is:

1. A hand-held instrument, comprising:
a handle portion;
an electrosurgical electrode supportably interconnected to and extending distally away from a first end of said handle portion in a first direction;
a signal cable, extending proximally from a proximal end of the handle portion to an interconnected coupler end that is provided to interface with an electrosurgical generator, for transmission of electrosurgical signals to the electrosurgical electrode via the signal cable;
at least one electrically-powered light source, interconnected to said handle portion, for emitting light in said first direction to illuminate a volume extending along the electrosurgical electrode from said first end of the handle portion to a distal end of the electrosurgical electrode;
at least one battery, disposed remotely from said handle portion, to provide electrical power to said at least one light source as a DC signal;
an electrical cable, extending proximally from the proximal end of the handle portion to an interconnected battery module for supporting said at least one battery, to provide said electrical power from said at least one battery to said at least one light source via the electrical cable; and
a switch, interconnected to said handle portion and in electrical communication with said at least one battery by said electrical cable, for selective activation of said at least one light source by said electrical power form said at least, one battery.

2. A hand-held instrument as recited in claim 1, wherein said battery module is provided for removably supporting said at least one battery.

3. A hand-held instrument as recited in claim 1, wherein said at least one battery comprises:
a battery pack having at least two batteries.

4. A hand-held instrument as recited in claim 1, wherein said at least one light source is one of a plurality of light sources for emitting light in said first direction.

5. A hand-held-instrument as recited in claim 4, wherein said plurality of light sources include at least three light sources disposed at spaced locations about an adjoinment region adjacent to a distal end of the handle portion and activatable.

6. A hand-held instrument as recited in claim 5, wherein said switch is provided for activation of said at least three light sources together.

7. A hand-held instrument as recited in claim 5, wherein said handle portion includes a contoured segment configured to restrict rolling of the hand-held instrument when disposed on a support surface.

8. A hand-held instrument as recited in claim 5, wherein said electrical cable is routed together with said signal cable.

9. A hand-held instrument as recited in claim 5, wherein each of said at least three light sources emits at least 1,000 mcd of light.

10. A hand-held instrument as recited in claim 5, wherein said at least three light sources are activatable to illuminate the entirety of said volume with at least 1,000 mcd of light.

11. A hand-held instrument as recited in claim 5, wherein different ones of said at least three light sources emit light at corresponding different predetermined wavelengths.

12. A hand-held instrument as recited in claim 11, wherein said at least three light sources emit light of a color temperature of at least 3,000K.

13. A hand-held instrument as recited in claim 5, further comprising:

a toggle member supportably interconnected to said handle portion and selectively manipulatable by a user to contact said switch for activation of said at least three light sources.

14. A hand-held instrument as recited in claim 13, wherein toggle member is depressible to activate said at least three light sources.

15. A hand-held instrument as recited in claim 5, wherein said signal cable and said electrical cable are routed within a common sheath to a distal end having said battery module adjoined to said coupler end.

16. A hand-held instrument as recited in claim 1, wherein said electrical cable is routed with said signal cable.

17. A hand-held instrument as recited in claim 16, wherein said signal cable and said electrical cable are routed within a common sheath to an end having said battery module adjoined to said coupler end.

18. A hand-held instrument as recited in claim 1, further comprising:
   an electrode socket, wherein said electrosurgical electrode is removable from and replaceable in said electrode socket.

19. A hand-held instrument as recited in claim 1, wherein said volume extends about at least a majority of the electrosurgical electrode.

20. A hand-held instrument as recited in claim 19, wherein said at least one light source is one of three light sources disposed at spaced locations about the handle portion, and further comprising:
   a light transmissive nose disposed about the three light sources.

* * * * *

UNITED STATES PATENT AND TRADEMARK OFFICE
CERTIFICATE OF CORRECTION

PATENT NO. : 10,136,960 B2
APPLICATION NO. : 14/997911
DATED : November 27, 2018
INVENTOR(S) : Richard P. Fleenor Page 1 of 1

It is certified that error appears in the above-identified patent and that said Letters Patent is hereby corrected as shown below:

In the Specification

Column 14, Line 29-delete "Wth" and insert therefore --"With"--
Column 18, Line 47-delete "Wth" and insert therefore --"With"--
Column 19, Line 33-delete "Wth" and insert therefore --"With"--

In the Claims

Column 32, Line 29-delete "form" and insert therefore --"from"--

Signed and Sealed this
Nineteenth Day of February, 2019

Andrei Iancu
*Director of the United States Patent and Trademark Office*